US009669243B2

(12) United States Patent
Dueva-Koganov et al.

(10) Patent No.: US 9,669,243 B2
(45) Date of Patent: *Jun. 6, 2017

(54) DELIVERY OF HYDROPHOBIC BENEFIT AGENTS FROM BODYWASHES AND THE LIKE ONTO A KERATINOUS SUBSTRATE

(75) Inventors: Olga V. Dueva-Koganov, White Plains, NY (US); Balint Koroskenyi, Peekskill, NY (US); Xian-Zhi Zhou, Leonia, NJ (US)

(73) Assignee: BASF SE, Ludwigshafen (DE)

( * ) Notice: Subject to any disclaimer, the term of this patent is extended or adjusted under 35 U.S.C. 154(b) by 567 days.

This patent is subject to a terminal disclaimer.

(21) Appl. No.: 12/386,716

(22) Filed: Apr. 22, 2009

(65) Prior Publication Data

US 2010/0135936 A1 Jun. 3, 2010

Related U.S. Application Data

(60) Provisional application No. 61/125,173, filed on Apr. 23, 2008.

(51) Int. Cl.
| | |
|---|---|
| *A61K 8/90* | (2006.01) |
| *A61K 47/30* | (2006.01) |
| *A61K 47/34* | (2006.01) |
| *A61Q 17/04* | (2006.01) |
| *A61Q 19/00* | (2006.01) |
| *A61K 31/01* | (2006.01) |
| *A61Q 19/10* | (2006.01) |
| *A61K 8/899* | (2006.01) |

(52) U.S. Cl.
CPC .............. *A61Q 19/10* (2013.01); *A61K 8/899* (2013.01); *A61Q 17/04* (2013.01)

(58) Field of Classification Search
USPC .......................................................... 424/59
See application file for complete search history.

(56) References Cited

U.S. PATENT DOCUMENTS

| | | | |
|---|---|---|---|
| 2,826,551 A | 3/1958 | Geen et al. | |
| 3,929,678 A | 12/1975 | Laughlin et al. | |
| 3,964,500 A | 6/1976 | Drakoff | |
| 4,364,837 A | 12/1982 | Pader | |
| 4,557,853 A | 12/1985 | Collins | |
| 4,707,293 A | 11/1987 | Ferro | |
| 5,338,539 A | 8/1994 | Raspanti | |
| 5,387,608 A | 2/1995 | Andrews | |
| 5,468,477 A | 11/1995 | Kumar et al. | |
| 5,518,713 A | 5/1996 | Raspanti | |
| 5,601,811 A | 2/1997 | Gallaher et al. | |
| 5,653,988 A | 8/1997 | Gerber et al. | |
| 5,760,136 A * | 6/1998 | Kato et al. | 525/100 |
| 5,980,872 A | 11/1999 | Luther et al. | |
| 6,201,093 B1 * | 3/2001 | Messner et al. | 528/28 |
| 6,280,757 B1 | 8/2001 | Mcatee et al. | |
| 6,313,256 B1 | 11/2001 | O'Lenick | |
| 6,365,672 B1 | 4/2002 | Adams et al. | |
| 6,379,655 B1 * | 4/2002 | Breton | A61K 8/41 424/400 |
| 6,383,500 B1 * | 5/2002 | Wooley et al. | 424/401 |
| 6,459,960 B1 | 10/2002 | Shuto et al. | |
| 6,524,614 B2 | 2/2003 | Cannell et al. | |
| 6,858,696 B2 | 2/2005 | Destarac et al. | |
| 6,861,397 B2 | 3/2005 | Seitz, Jr. et al. | |
| 6,998,113 B1 | 2/2006 | Traynor et al. | |
| 7,025,952 B1 | 4/2006 | Traynor et al. | |
| 7,037,513 B1 | 5/2006 | Traynor et al. | |
| 7,105,579 B2 | 9/2006 | Adam et al. | |
| 7,226,581 B2 | 6/2007 | Traynor et al. | |
| 7,232,561 B2 | 6/2007 | Dubief et al. | |
| 2003/0223948 A1 * | 12/2003 | Maubru | A61K 8/604 424/70.13 |
| 2004/0009136 A1 | 1/2004 | Dubief et al. | |
| 2004/0039101 A1 | 2/2004 | Dubief et al. | |

(Continued)

FOREIGN PATENT DOCUMENTS

| | | |
|---|---|---|
| CN | 1137923 | 8/1997 |
| EP | 0 582 189 A2 | 2/1994 |

(Continued)

OTHER PUBLICATIONS

Lima, L. M.; Barriero, E. J. "Bioisosterism: A useful strategy for Molecular Modification" Current Medicinal Chemistry, 2005, vol. 12, pp. 23-49.*
English Abstract of DE 10036694 which is equivalent to WO02/10501.
International Search Report dated: Feb. 2, 2010. References listed (excluding ones listed on this form) have previously been submitted.
Ying Jun Du and john L Brash "Synthesis and characterization of thiol-terminated poly(ethylene oxide) for chemisorption to gold surface" ,2003 Journal of Applied Polymer Science.
B.L. Diffey "A method for broad spectrum classification of sunscreens" International Journal of Cosmetic Science 16,47-52 (1994).

*Primary Examiner* — Mina Haghighatian
*Assistant Examiner* — Erin Hirt
(74) *Attorney, Agent, or Firm* — Lowenstein Sandler LLP

(57) ABSTRACT

This invention relates to a delivery system for hydrophobic benefit agents to keratinous substrates. The delivery system comprises amphiphilic block copolymers, and a hydrophobic benefit agent, which amphiphilic block copolymers comprise a siloxane segment and a cationic segment. The invention also relates to methods of delivering the hydrophobic benefit agents to the keratinous substrate. Furthermore, the delivery systems and methods of delivery are effective in retaining an hydrophobic benefit agents on the keratinous substrate after rinsing.

More particularly, the delivery systems are especially suitable in personal cleansing, body wash or rinse off lotion compositions and comprise certain amphiphilic polymers which effectively deposit the hydrophobic benefit agents onto a keratinous substrate, such as skin or hair.

20 Claims, No Drawings

(56) References Cited

U.S. PATENT DOCUMENTS

| | | |
|---|---|---|
| 2004/0091434 A1* | 5/2004 | Chodorowski-Kimmes et al. .............................. 424/59 |
| 2004/0202634 A1 | 10/2004 | L'Alloret |
| 2004/0223929 A1 | 11/2004 | Clapp et al. |
| 2005/0053569 A1 | 3/2005 | Bavouzet et al. |
| 2005/0079301 A1* | 4/2005 | Hartleben ............. C08F 283/12 428/34.1 |
| 2006/0123564 A1 | 6/2006 | Nishizawa et al. |
| 2008/0199418 A1 | 8/2008 | Koroskenyi et al. |
| 2008/0213322 A1 | 9/2008 | Birman et al. |
| 2010/0303750 A1 | 12/2010 | Koroskenyi et al. |

FOREIGN PATENT DOCUMENTS

| | | | |
|---|---|---|---|
| EP | 0 613 893 A1 | 9/1994 | |
| EP | 0 709 080 A1 | 5/1996 | |
| EP | 1 568 353 A1 | 8/2005 | |
| EP | 1568853 | 8/2005 | |
| GB | 849433 A | 9/1960 | |
| JP | 1995002964 | 3/1997 | |
| JP | 2000191450 | 7/2000 | |
| JP | 1998291967 | 10/2001 | |
| JP | 2009031145 A | 2/2009 | |
| WO | 97/00851 A1 | 1/1997 | |
| WO | 9932539 | 7/1999 | |
| WO | 0210501 | 2/2002 | |
| WO | 2008095822 | 8/2008 | |
| WO | WO2008/095822 | * 8/2008 | ............... A61K 8/89 |

\* cited by examiner

DELIVERY OF HYDROPHOBIC BENEFIT AGENTS FROM BODYWASHES AND THE LIKE ONTO A KERATINOUS SUBSTRATE

This application claims benefit under 35 USC 119(e) of U.S. Provisional app. No. 61/125,173, filed on Apr. 23, 2008, which is incorporated entirely herein by reference.

FIELD OF THE INVENTION

This invention relates to a delivery system for hydrophobic benefit agents to keratinous substrates. The delivery system comprises amphiphilic block copolymers, and a hydrophobic benefit agent, which amphiphilic block copolymers comprise a siloxane segment and a cationic segment. The invention also relates to methods of delivering the hydrophobic benefit agents to the keratinous substrate. Furthermore, the delivery systems and methods of delivery are effective in retaining an hydrophobic benefit agents on the keratinous substrate after rinsing.

More particularly, the delivery systems are especially suitable in personal cleansing, body wash or rinse off lotion compositions and comprise certain amphiphilic polymers which effectively deposit the hydrophobic benefit agents onto a keratinous substrate, such as skin or hair.

BACKGROUND

Body rinse off compositions are well known in the art. Body rinse off compositions may for example be a body wash which is primarily used to remove oil and dirt from the skin. Rinse off lotions may be used when showering or bathing. The purpose of rinse off lotions is to soften and condition the skin. Body wash compositions traditionally contain surfactants for cleansing purposes wherein the surfactants may irritate or remove natural oils from the skin. Body washes are known to contain hydrophobic agents such as petrolatum, which may mitigate the effects of irritating surfactants on the skin. However, the body wash is normally rinsed from the skin and with it much of the hydrophobic benefit agent. Body rinse off compositions, sometimes referred to as rinse off lotions are also subject to the same result. The rinsing of the lotion or body wash reduces the amount of residual hydrophobic benefit agent left on the skin.

There are a great many examples in the patent literature wherein hydrophobic benefit agents are incorporated as part of a body rinse off composition in attempts to provide moisturizing residual effects on the skin. U.S. Pat. No. 5,653,988 is an example of the use of hydrophobic benefit agents in a body wash and discloses anhydrous gelled oil compositions for use in cleansing. U.S. Pat. No. 4,707,293 also discloses a body cleanser consisting essentially of oil and saccharose ester and at least one other emulsifying agent and claims to effectively cleanse and leave a protecting lipid layer on the skin.

One of the known strategies for depositing hydrophobic benefit agents onto a keratinous surface is to use cationic polymers as a deposition aid. For example, U.S. Pat. No. 6,524,614 discloses delivery systems for water-insoluble ingredients containing organic phospholipid at least one amphoteric surfactant, at least one cationic polymer. The cationic polymer functions to control the amount of water insoluble ingredient deposited on a keratinous surface. The water insoluble ingredient may be a lipophilic ingredient such as a silicone, vitamin, natural oil or a sunscreen.

U.S. Pat. Nos. 7,226,581, 6,998,113 and 7,037,513 and 7,025,952 disclose body washes which contain sunscreen agents. Said sunscreen agents are frequently hydrophobic or water-insoluble. The cited patents allege that significant sun protection remains on the skin even after rinsing. The use of a cationic polymer is disclosed as an aid in helping the deposition of the sunscreen agent.

Furthermore, amphiphilic block copolymers are generally known for use in cosmetics. amphiphilic block copolymers generally comprise at least hydrophobic and hydrophilic polymeric segments and are described in U.S. Application Nos. 2004/0039101, 2004/0009136 and 2004/0202634 and U.S. Pat. Nos. 7,105,579, 7,232,561 all herein incorporated entirely by reference.

U.S. Application Publication No. 2005/0053569 discloses the use of amphiphilic block copolymers comprising at least a non-ionic hydrophobic block and at least a cationic block in conditions of use to assist in deposition of an emulsion on a keratinous surface.

Additionally, cationic functionalized polysiloxanes are known and are disclosed in Japanese unexamined Application Nos. JP1995002964 and JP1998291967 and PCT Application No. WO99/32539. These modified polysiloxanes are known for use as conditioning agents in hair bleach or dye compositions such as disclosed in U.S. Application Publication No. 2006/0123564 herein incorporated entirely by reference.

Block copolymers formed from polysiloxanes and polycationic segments are known and are described in U.S. Pat. No. 5,760,136 herein incorporated entirely by reference.

U.S. Pat. No. 5,468,477 discloses cosmetic compositions containing vinyl-silicone grafted copolymers herein incorporated entirely be reference.

Co-pending U.S. Publication No. 2008/0199418, filed Feb. 6, 2007 discloses amphiphilic block copolymer comprising polysiloxane and polycationic blocks which are used in conditioning shampoos and herein incorporated entirely by reference.

However, there is still a need for alternative delivery systems for hydrophobic benefit agents to keratinous substrates which work effectively to retain the hydrophobic benefit agent on the substrate even after rinsing.

SUMMARY OF THE INVENTION

The present invention encompasses several compositional embodiments.

The first compositional embodiment is directed to a cosmetically acceptable delivery system for hydrophobic benefit agents to a keratinous substrate wherein the delivery system comprises i.) an amphiphilic block copolymer, which amphiphilic block copolymer comprises a hydrophilic (A) block and a hydrophobic (B) block, wherein the hydrophilic block (A) comprises at least a cationic monomer unit or a potentially cationic monomer unit in the conditions of use and the unit is represented by formulae (I) or (II)

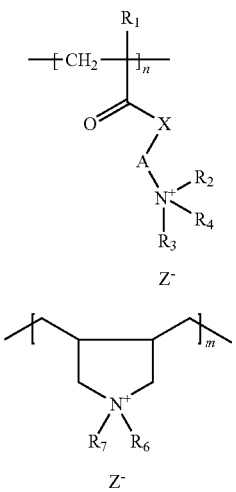

(I)

(II)

wherein $R_1$ is hydrogen or methyl,
$R_2$ is hydrogen, a branched or unbranched $C_{1-4}$ alkyl,
$R_3$ and/or $R_4$ are independently branched or unbranched $C_{1-22}$ alkyl, $C_1$-$C_4$ alkylhydroxy, benzyl
or
$R_3$ and $R_4$ can be combined to form a five or six membered ring with the nitrogen, said ring containing one or more hetero atoms,
$Z^-$ is the conjugate base of an acid,
X is oxygen or —$NR_5$,
wherein $R_5$ is as defined in $R_1$ above,
A is an alkylene group of 1 to 4 carbons,
$R_6$ and $R_7$ are hydrogen, branched or unbranched $C_{1-22}$ alkyl, benzyl or $C_1$-$C_4$ alkylhydroxy,
n and m are 2, 3, 4 or greater;
and
the hydrophobic polymeric block (B) comprises siloxane monomer units,
and
ii.) a hydrophobic benefit agent.

A second compositional embodiment encompasses a body rinsable composition comprising:
i.) an amphiphilic block copolymer comprising at least an A block and a B block as defined above,
and
ii.) a hydrophobic benefit agent.

The hydrophobic B block may for example comprise siloxane monomer units of formula (III)

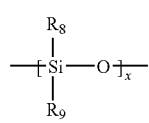

(III)

$R_8$ and $R_9$ are independently $C_{1-4}$alkyl, phenylalkyl, alkoxy, aryl, aryloxy, alkylaryl, alkylamine, alkylhydroxy, polyoxyalkylene, polyalkylene polyamine or —R-L-Polycationic Block,
R is $C_1$ to $C_{10}$ alkylene, arylene, alkarylene or alkoxyalkylene,
wherein the Polycationic block is defined as block A above,
L is a linking group,
and
x is and integer from 2 to 10,000.

For example,

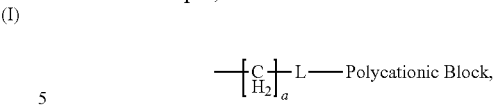

wherein the Polycationic block is defined as above,
L is a linking group and
a is an integer from 1 to 12.

A body rinsable composition is any composition which is used on the skin and then rinsed. Thus the composition may be a body wash, shower cream, shower gel, liquid soap or a bar soap.

The invention also embodies a method of delivering a hydrophobic benefit agent to a keratinous substrate which method comprises the steps of
forming a mixture comprising said hydrophobic benefit agent with the amphiphilic block copolymer described above,
applying the mixture to the keratinous substrate
and
rinsing said mixture from the keratinous substrate,
wherein an effective amount of the hydrophobic benefit agent is retained on the keratinous substrate.

An effective amount of hydrophobic benefit agent retained on the keratinous substrate as used herein means at least about 1 to about 50 wt. % of the total benefit agent applied to the substrate is retained.

The composition may be in the form of a simple or complex (O/W, W/O, O/W/O or W/O/W) emulsion such as a cream, a milk, a gel, a gel cream, clear liquid or a lotion specifically designated for in-shower use.

"Cosmetically acceptable" means a non-toxic, non-irritating delivery system which is suitable for application on skin.

The symbol * indicates that there is a binding site at the position marked with * unless otherwise specified.

DETAILED DESCRIPTION OF THE INVENTION

All percentages, parts and ratios are based upon the weight unless otherwise specified. All such weights as they pertain to listed ingredients are based on the active level and, therefore, do not include carriers or by-products that may be included in commercially available materials, unless otherwise specified.

Delivery System

A delivery system for purposes of the invention, refers to a system which effectively delivers a hydrophobic benefit agent to skin or hair. The delivery system requires the presence of the amphiphilic block copolymer described above in combination with the benefit agent, wherein an effective amount of the hydrophobic benefit agent is retained on the keratinous substrate after rinsing.

A rinsable compositions, as used herein, means a composition designed to be rinsed off by a liquid such as water. After the composition is rinsed off, the hydrophobic benefit agent(s) are at least in part retained on the keratinous substrate.

Keratinous Substrate

Keratinous substrate is hair, skin, finger nails or toe nails.

Hydrophobic Benefit Agent

The hydrophobic benefit agent may be any water insoluble substance which benefits the keratinous substrate.

Thus, for example, the benefit agent may be any material which retards the decrease in water content from skin (stratum corneum) or hair. Thus silicone oils, a waxes, petrolatum, linear or branched oils, water insoluble or slightly soluble organic sunscreens, micronized sunscreens, lipids, ester oils, water insoluble or slightly soluble vitamin or vitamin derivatives, plant extracts or hydrophobically modified pigments.

Water insoluble as used herein means that the agent is substantially insoluble in cold and hot water. For example, the United States Pharmacopeia defines insoluble as less than 100 microgram per mL (0.01%). For purposes of the invention, substantially insoluble means a solubility in water of less than 0.2 wt. %.

The hydrophobic benefit agent is not a surfactant.

Silicone Oils

Thus, hydrophobic benefit agents would include such substances as silicone oils, gums and modifications thereof such as linear and cyclic polydimethyl siloxane, organo functional silicones (alkyl and alkyl aryl), and amino silicones.

Waxes

Waxes such as lanolin and beeswax are also considered hydrophobic benefit agents as used herein.

Linear and Branched Oils

Skin compatible oils suitable as the hydrophobic benefit agent may be liquid and semi-solid hydrocarbons. These include linear and branched oils such as liquid paraffin, squalene, squalane, mineral oil, low viscosity synthetic hydrocarbons such as polyalphaolefin sold by ExxonMobil under the trade name of PURESYN PAO and polybutene under the trade name PANALANE or INDOPOL. Light (low viscosity) highly branched hydrocarbon oils are also suitable.

Petrolatum

Petrolatum is a unique hydrocarbon material and a useful component of the present invention. Its semi-solid nature can be controlled both in production and by the formulator through blending with other oils.

Ester Oils

Other agents are for example, higher fatty acids and higher fatty alcohols, both saturated and unsaturated, having a carbon chain length in the range of $C_{12}$ to $C_{30}$, esters oils. Ester oils, as the name implies, have at least one ester group in the molecule. One type of common ester oil useful in the present invention are the fatty acid mono and polyesters such as cetyl octanoate, octyl isonanoanate, myristyl lactate, cetyl lactate, isopropyl myristate, myristyl myristate, isopropyl palmitate, isopropyl adipate, butyl stearate, decyl oleate, cholesterol isostearate, glycerol monostearate, glycerol distearate, glycerol tristearate, alkyl lactate, alkyl citrate and alkyl tartrate; sucrose ester and polyesters, sorbitol ester, and the like.

Another type of useful ester oil is predominantly comprised of triglycerides and modified triglycerides. These include vegetable oils such as jojoba, soybean, canola, sunflower, safflower, rice bran, avocado, almond, olive, sesame, persic, castor, coconut, primrose and mink oils. Synthetic triglycerides can also be employed. Modified triglycerides include materials such as ethoxylated and maleated triglyceride derivatives. Proprietary ester blends such as those sold by Finetex as Finsolv are also suitable, as is ethylhexanoic acid glyceride.

Lipids

Lipids such as cholesterol, ceramides, sucrose esters and pseudo-ceramides are envisioned as hydrophobic benefit agents;

Vitamins

Water insoluble or slightly soluble family or derivatives of vitamins, flavonoids and carotenoids are considered hydrophobic benefit agents. Specific examples considered are Vitamin A or the family of retinoids and derivatives. Specific examples would include esters such as retinyl palmitate or retinyl acetate, retinal, retinol or retinoic acid.

Vitamin E or the family of fat soluble vitamins with antioxidant properties such as tocopherols and tocotrienols;

Vitamin D or the family of fat-soluble prohormones such as vitamin $D_2$ (or ergocalciferol) and vitamin $D_3$ (or cholecalciferol);

Vitamin K or the family of lipophilic, hydrophobic vitamins which are chemically 2-methyl-1,4-naphthoquinone derivatives;

Cartenoids such as beta-carotene, canthaxanthin, zeaxanthin, lycopen, lutein, crocetin, capsanthin, cyanidin, xanthophyll and astaxanthin;

Flavonoids such rutin, quercetin, hesperidin, diosmin, isoquercitrin, hespeddin, naringin, and methylhesperidin.

Cartenoids and flavonoids are active at low levels. These may for example be used at levels as low as 0.001 wt. % to 1.0% or 0.01 to about 0.1 wt %. As cartenoids and flavonoids as active at low level and colored it may be preferable to use at levels between 0.001 to about 0.05 wt. %.

Vitamins such as vitamin E may be used at higher concentrations. Thus for example, vitamin concentration may vary anywhere from 0.001 to about 5 wt. % based on the weight of the total formulation.

Plant Extracts and Seed Extracts

Water insoluble or slightly water soluble plant (including seed extract such as neem seed oil) extracts are for example willowherb extract; potato extracts such as DERMOLECTINE and CAPILECTINE; mistletoe extract; avocado extract; wheat germ extract; kidney bean extract; other vegetable extracts such as carrot, soybean, oat, beet, cucumber, broccoli, pumpkin and tomato extract; tobacco extract; other herbal extracts such as dill, horseradish, weeping willow, ginseng, poppy, or sesame; other fruit extracts such as orange, lemon, watermelon, banana, and coconut.

Plant extracts and seed extracts are for example, used in amounts ranging from be 0.01 to about 10 wt. % based on the total weight of the formulation applied as a delivery system, of rinsable composition.

Organic Sunscreens

Water insoluble or slightly soluble organic sunscreens include UV absorbers. The UV absorbers may be a UVB or UVA absorber or a combination of UVB and UVA absorbers.

The water insoluble or slightly soluble organic sunscreens may be non-micronized micronized or micronizable. Alternatively, the sunscreen may be a water insoluble or slightly soluble oil.

Suitable insoluble or slightly water soluble organic sunscreens or UV absorbers as hydrophobic benefit agents may be chosen from the chemical classes such as triazines, benzotriazoles, benzophenones, vinyl group-containing amides, cinnamic acid amides or sulfonated benzimidazoles UV absorber.

The class of triazine compounds may, for example be represented by the formula

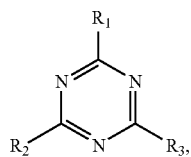
(1)

wherein
$R_1$, $R_2$ and $R_3$, independently from each other, are hydrogen; hydroxy; $C_1$-$C_3$alkoxy; $NH_2$; $NHR_4$; $N(R_4)_2$; $OR_4$; $C_6$-$C_{12}$aryl; phenoxy; anilino; pyrrolo; in which the respective phenyl, phenoxy, anilino or pyrrolo moieties are not substituted or substituted by one, two or three substitutents selected from OH, carboxy, CO—$NH_2$, $C_1$-$C_{12}$alkyl, $C_1$-$C_{12}$alkoxy, a methylidenecamphor group, a group —(CH=CH)$_m$C(=O)—$OR_4$, a group

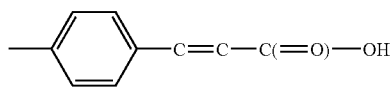

or the corresponding alkali metal, ammonium, mono-, di- or tri-$C_1$-$C_4$alkylammonium, mono-, di- or tri-$C_2$-$C_4$alkanolammonium salts, or the $C_1$-$C_3$alkyl esters thereof or by a radical of formula

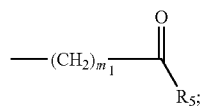
(1a)

$R_4$ is $C_1$-$C_5$alkyl;
$R_5$ is hydroxy; $C_1$-$C_5$alkyl that is unsubstituted or substituted by one or more OH groups; $C_1$-$C_5$alkoxy; amino; mono- or di-$C_1$-$C_5$alkylamino; M; a radical of formula

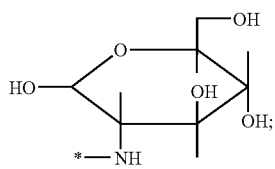
(1b)

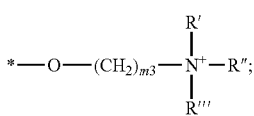
(1c)

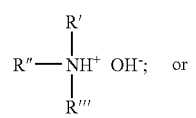
(1d)

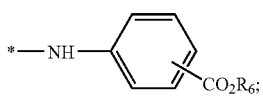
(1e)

R', R" and R'" independently of the other are $C_1$-$C_{14}$alkyl that is unsubstituted or substituted by one or more OH groups;

$R_6$ is hydrogen; M; $C_1$-$C_5$alkyl; or a radical of the formula

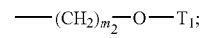

M is a metal cation;
$T_1$ is hydrogen; or $C_1$-$C_8$alkyl;
m is 0 or 1;
$m_1$ is from 1 to 5;
$m_2$ is from 1 to 4; and
$m_3$ is from 2 to 14.

Compounds of formula (1) may be those, wherein
$R_1$, $R_2$ and $R_3$ independently from each other are a radical of formula

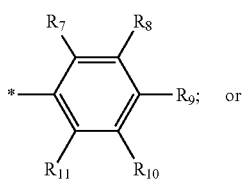
(1f)

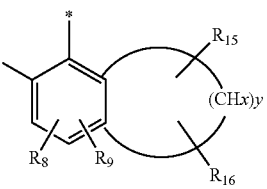
(1g)

$R_7$ and $R_{11}$ independently from each other are hydrogen; $C_1$-$C_{18}$alkyl; or $C_6$-$C_{12}$aryl;
$R_8$, $R_9$ and $R_{10}$, independently from each other, are hydrogen; or a radical of formula

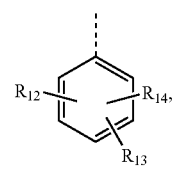
(1h)

wherein, in formula (1f), at least one of the radicals $R_8$, $R_9$ and $R_{10}$ are a radical of formula (1h);
$R_{12}$, $R_{13}$, $R_{14}$, $R_{15}$ and $R_{16}$ independently from each other are hydrogen; hydroxy; halogen; $C_1$-$C_{18}$alkyl; $C_1$-$C_{18}$alkoxy; $C_6$-$C_{12}$aryl; biphenylyl; $C_6$-$C_{12}$aryloxy; $C_1$-$C_{18}$alkylthio; carboxy; —COOM; $C_1$-$C_{18}$-alkylcarboxyl; aminocarbonyl; or mono- or di-$C_1$-$C_{18}$alkylamino; $C_1$-$C_{10}$acylamino; —COOH;
M is an alkali metal ion;
x is 1 or 2; and
y is a number from 2 to 10.

More specific examples of triazine derivatives are compounds of formula (2)

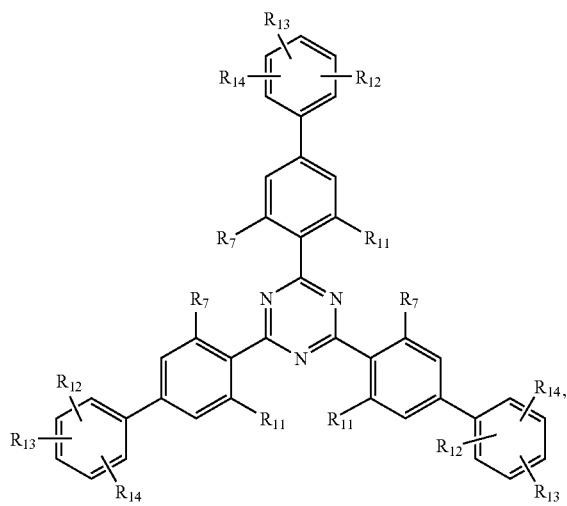

wherein
$R_7$, $R_{11}$, $R_{12}$, $R_{13}$ and $R_{14}$ are defined as in formula (1f), (1g) or (1h), and most preferably compound of formula (2), wherein
$R_7$ and $R_{11}$ are hydrogen.

Furthermore, triazine derivatives of formula (3)

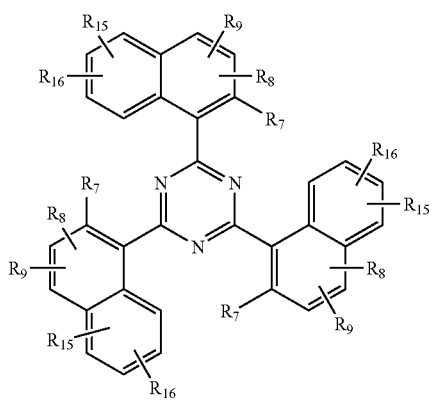

are preferred, wherein
$R_7$, $R_8$, $R_9$, $R_{15}$ and $R_{16}$ are defined as in formula (1g), and most preferably compounds of formula (3), wherein
$R_7$, $R_8$, $R_9$, $R_{15}$ and $R_{16}$ are hydrogen; or, independently from each other, $C_1$-$C_{18}$alkyl.

Most preferred as component (a) are triazine derivatives of formula (4)

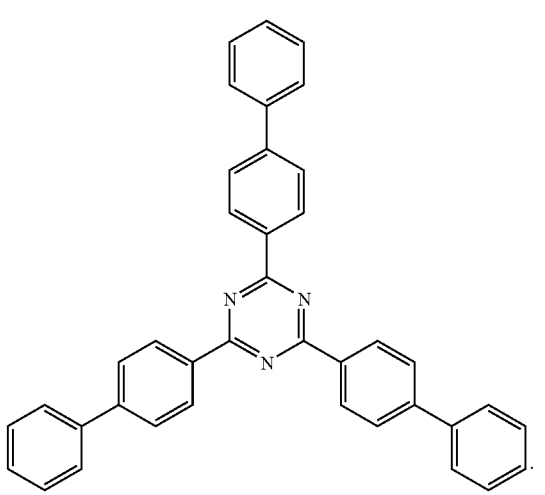

Further preferred triazine derivatives correspond to formula (5)

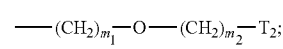

wherein
$R_{17}$ and $R_{18}$, independently of one another, are $C_1$-$C_{18}$alkyl; $C_2$-$C_{18}$alkenyl; a radical of the formula —$CH_2$—CH(—OH)—$CH_2$—O-$T_1$; or a radical of the formula

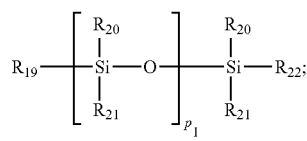

a radical of the formula (5a)

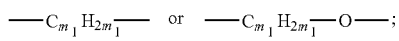

$R_{19}$ is a direct bond; a straight-chain or branched $C_1$-$C_4$alkylene radical or a radical of the formula —$C_{m_1}H_{2m_1}$—  or  —$C_{m_1}H_{2m_1}$—O—;

$R_{20}$, $R_{21}$ and $R_{22}$, independently of one another, are $C_1$-$C_{18}$alkyl; $C_1$-$C_{18}$alkoxy or a radical of the formula

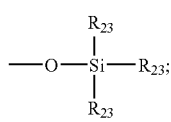

R$_{23}$ is C$_1$-C$_5$alkyl;

T$_1$ and T$_2$, independently from each other, are hydrogen; or C$_1$-C$_8$alkyl;

m$_1$, m$_2$ and m$_3$, independently of one another, are 1 to 4;

p$_1$ is 0; or a number from 1 to 5;

A$_1$ is a radical of the formula (5b)

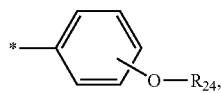

(5c)

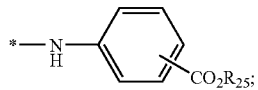

or of the formula (5d)

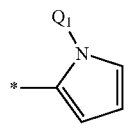

R$_{24}$ is hydrogen; C$_1$-C$_{10}$alkyl, —(CH$_2$CHR$_{26}$—O)$_{n_1}$—R$_{25}$; a —CH$_2$—CH(—OH)—CH$_2$—O-T$_1$; or radical of the formula

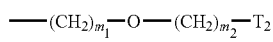

R$_{25}$ is hydrogen; M; C$_1$-C$_5$alkyl; or a radical of the formula

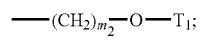

R$_{26}$ is hydrogen; or methyl;

Q$_1$ C$_1$-C$_{18}$ alkyl;

M is a metal cation; and n$_1$ is 1-16.

Further triazine examples are given below by formulae (5e)

(5f)

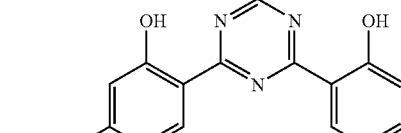

the formula (5g)

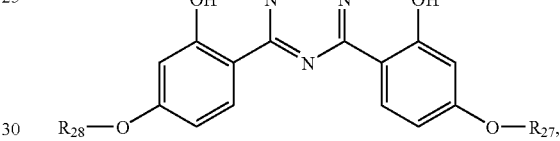

(5h)

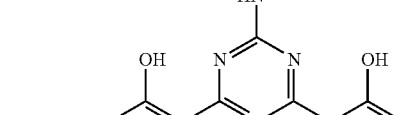

in which

R$_{27}$ and R$_{28}$, independently of one another, are C$_3$-C$_{18}$alkyl; or —CH$_2$—CH(—OH)—CH$_2$-O-T$_1$;

$R_{30}$ is $C_1$-$C_{10}$alkyl or a radical of the formula

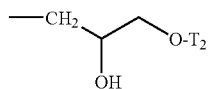
(5a₁)

or the formula

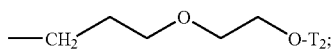
(5a₂)

$R_{30}$ is hydrogen; M; $C_1$-$C_5$alkyl; —NH—$C_1$-$C_5$alkyl, preferably —NH-tert.alkyl; or a radical of the formula —$(CH_2)_m$—O-$T_2$;

$T_1$ and $T_2$, independently of one another, are hydrogen; or $C_1$-$C_5$alkyl; and m is 1 to 4.

Compounds of the formulae (5e) and (5f), in which
$R_{27}$ and $R_{28}$, independently of one another, are $C_3$-$C_{18}$alkyl; or —$CH_2$—CH(—OH)—$CH_2$—O-$T_1$;
$R_{29}$ is $C_1$-$C_{10}$alkyl;
and compounds of the formulae (5g) and (5h), in which
$R_{27}$ and $R_{28}$, independently of one another, are $C_3$-$C_{18}$alkyl or —$CH_2$—CH(—OH)—$CH_2$—O-$T_1$; and
$T_1$ is hydrogen; or $C_1$-$C_5$alkyl are of interest.

Furthermore, interesting triazines correspond to the formula

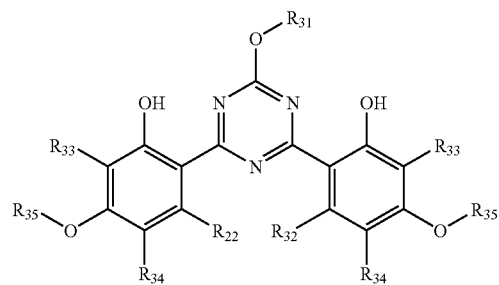
(6)

in which
$R_{31}$ is $C_1$-$C_{30}$alkyl; $C_2$-$C_{30}$alkenyl; unsubstituted or $C_1$-$C_5$alkyl-mono- or polysubstituted $C_5$-$C_{12}$cycloalkyl, $C_1$-$C_5$alkoxy-$C_1$-$C_{12}$alkyl; amino-$C_1$-$C_{12}$alkyl; $C_1$-$C_5$monoalkylamino-$C_1$-$C_{12}$alkyl; $C_1$-$C_5$dialkylamino-$C_1$-$C_{12}$alkyl; a radical of the formula

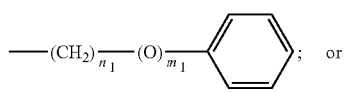
(6a)

or

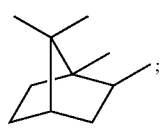
(6b)

$R_{32}$, $R_{33}$ and $R_{34}$, independently of one another, are hydrogen; hydroxyl; $C_1$-$C_{30}$alkyl; or $C_2$-$C_{30}$alkenyl;

$R_{35}$ is hydrogen; or $C_1$-$C_5$alkyl;
$m_1$ is 0 or 1; and
$n_1$ is 1 to 5.

Preferred compounds correspond to the formula

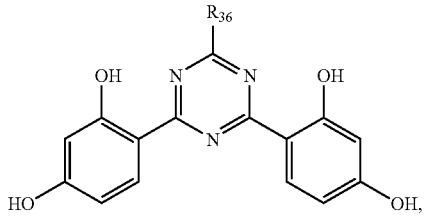
(7)

wherein
$R_{36}$ is

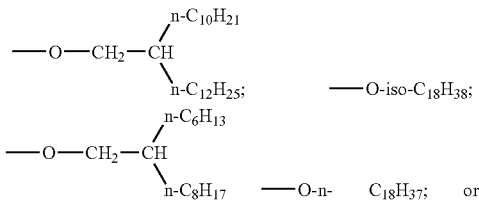

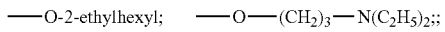

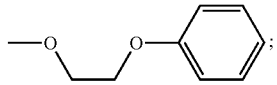 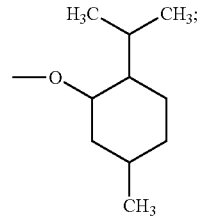

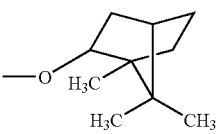 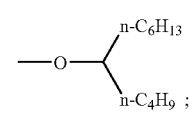

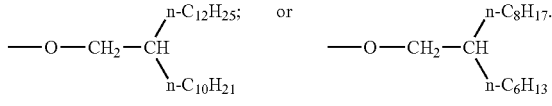

Further preferred triazine derivatives as the hydrophobic benefit agent are those compounds having one of the formulae

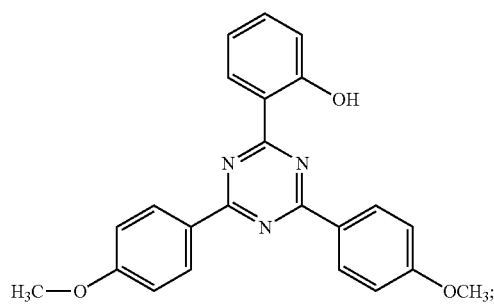
(8)
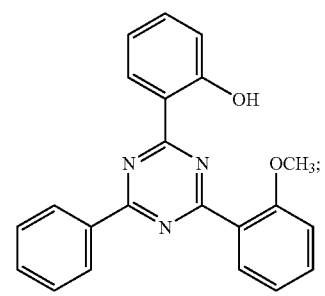
(9)
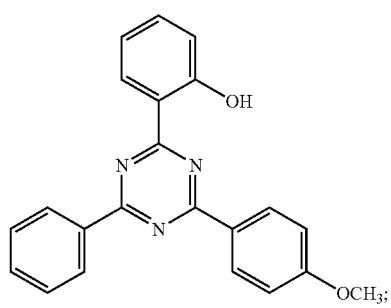
(10)
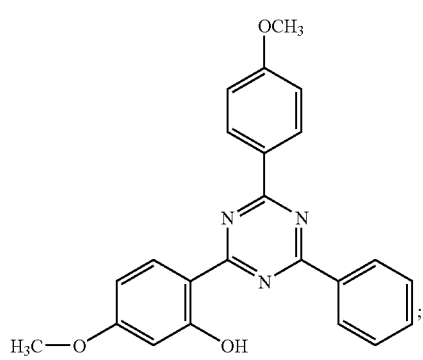
(11)
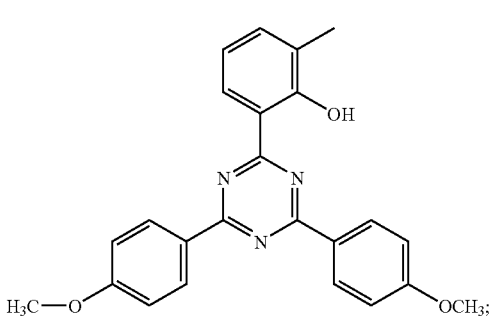
(12)
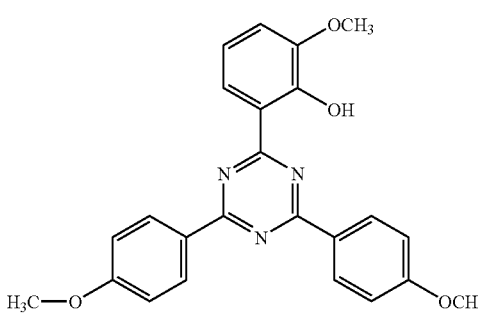
(13)
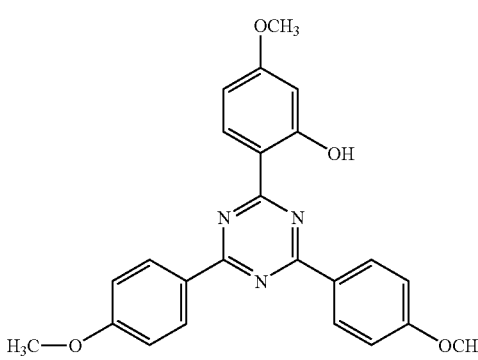
(14)
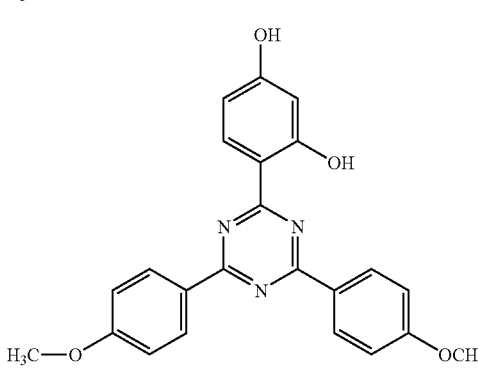
(15)
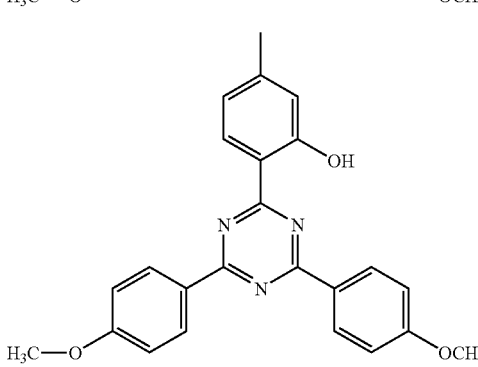
(16)
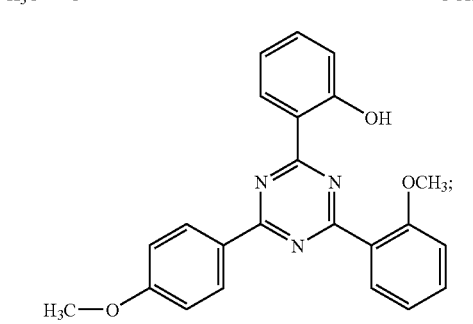
(17)

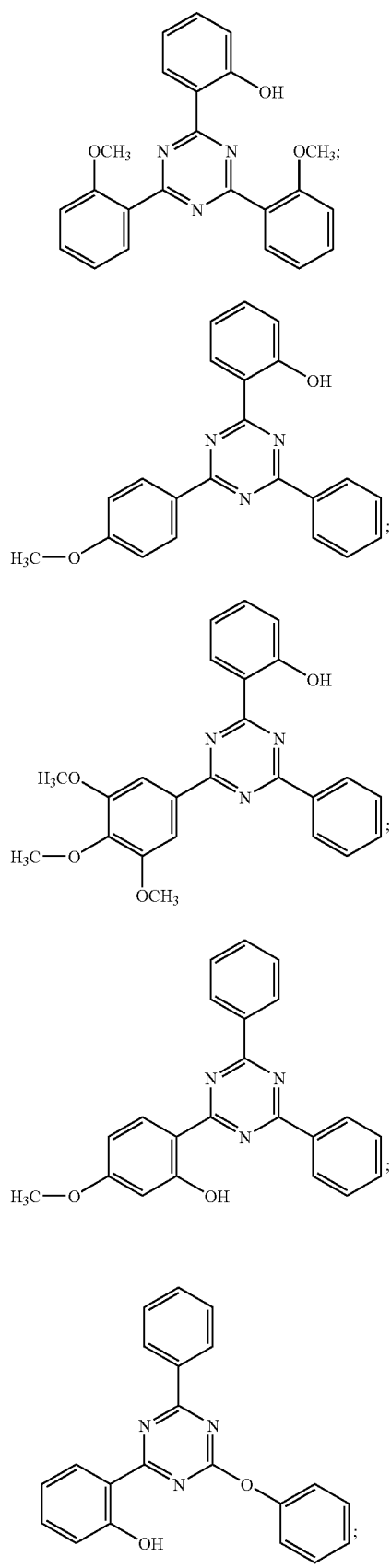
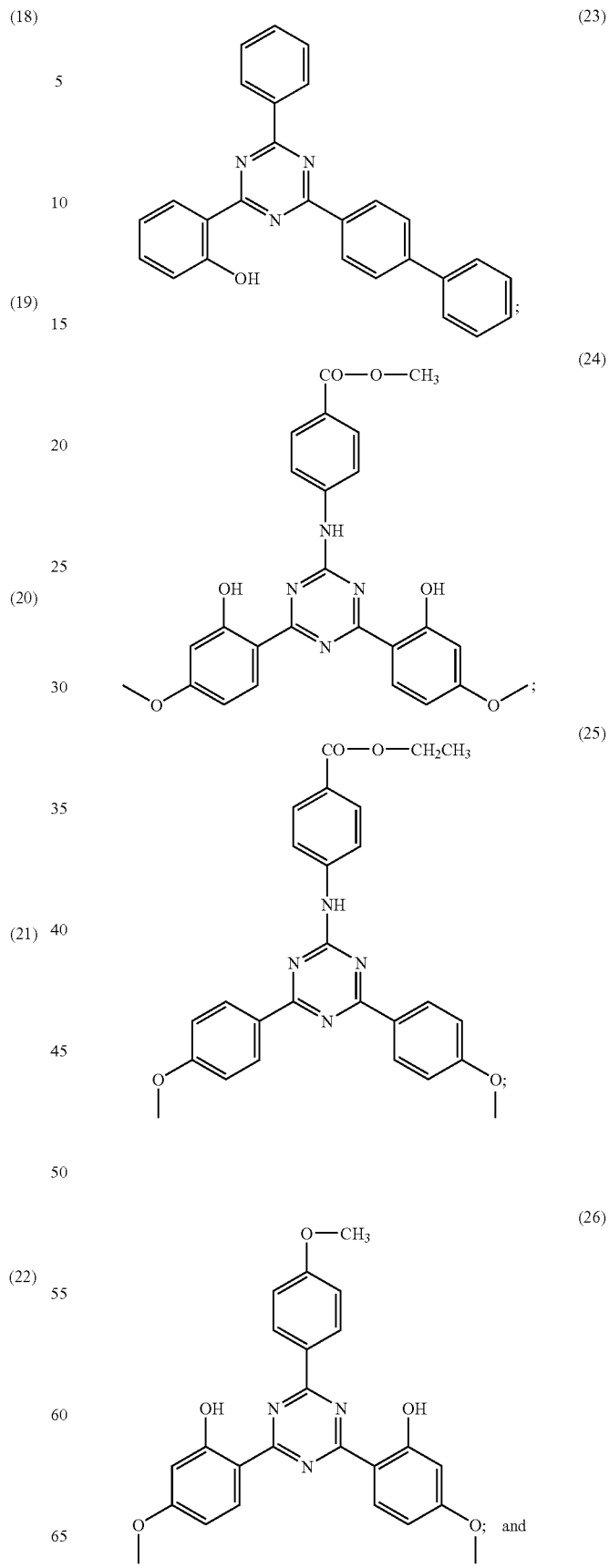

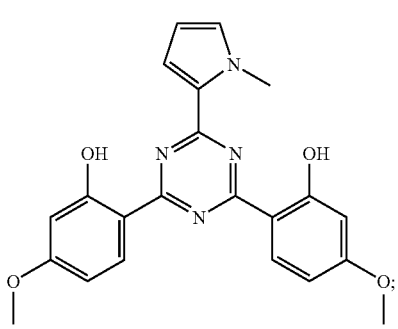

(27)

as well as 2,4,6-tris(diisobutyl-4'-aminobenzalmalonate)-s-triazine and 2,4-bis(diisobutyl-4-aminobenzalmalonate)-6-(4'-aminobenzylidenecamphor)-s-triazine.

Particularly preferred compounds of formula (1) are those having the formula:

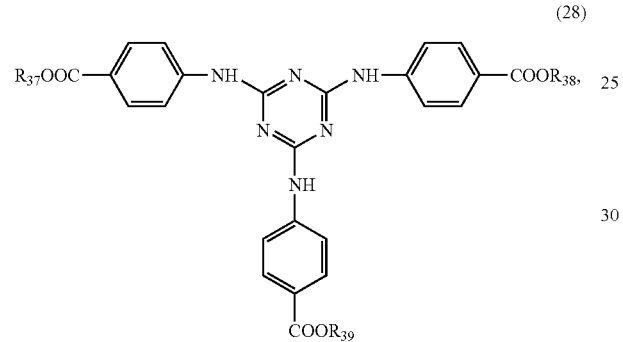

(28)

wherein
$R_{37}$, $R_{38}$ and $R_{39}$, independently from each other are hydrogen; an alkali metal; or an ammonium group $N^+(R_{40})_4$;
$R_{40}$ is hydrogen; or an organic radical; $C_1$-$C_3$alkyl; or a polyoxyethylene radical which contains from 1 to 10 ethylene oxide units and the terminal OH group of which may be etherified by a $C_1$-$C_3$alcohol.

In relation to the compounds of formula (28), when $R_{37}$, $R_{38}$ and $R_{39}$ is an alkali metal it is preferably potassium or, especially sodium; when $R_{37}$, $R_{38}$ and $R_{39}$ is a group $N(R_{40})_4$ in which $R_{30}$ has its previous significance, it is preferably a mono-, di- or tri-$C_1$-$C_4$alkylammonium salt, a mono-, di- or tri-$C_2$-$C_4$alkanolammonium salt or a $C_1$-$C_3$alkyl ester thereof; when $R_{40}$ is a $C_1$-$C_3$alkyl group, it is preferably a $C_1$-$C_2$alkyl group, more preferably a methyl group; and when $R_{30}$ is polyoxyethylene group, this preferably contains from 2-6 ethylene oxide units.

The benzotriazole organic UV absorbers hydrophobic benefit agent for example may have the formula

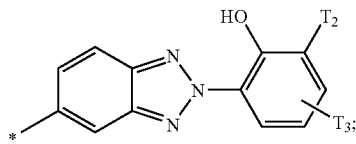

(29)

wherein
$T_1$ is $C_1$-$C_3$alkyl or, preferably, hydrogen; or a radical of formula (29a)

and
$T_2$ and $T_3$, independently from each other are $C_1$-$C_{12}$alkyl, preferably i-octyl; or $C_1$-$C_4$alkyl substituted by phenyl, preferably α,α-dimethylbenzyl.

Additionally, the class of benzotriazole organic UV absorbers corresponding to the formula (30) below are important.

(30)

wherein
$T_2$ has its previous significance.

A still further class of benzotriazole organic UV absorbers of interest corresponds to the formula (31)

wherein
$T_2$ is hydrogen; $C_1$-$C_{12}$alkyl, preferably iso-octyl, or $C_1$-$C_4$alkyl substituted by phenyl, preferably α,α-dimethylbenzyl.

The class of vinyl group-containing amide organic UV absorbers is for example, represented by formula:

$$R_{41}-(Y)_m-CO-C(R_{42})=C(R_{43})-N(R_{44})(R_{45}),$$
wherein (32)

$R_{41}$ is $C_1$-$C_3$alkyl, preferably $C_1$-$C_2$alkyl, or phenyl optionally substituted by one, two or three substituents selected from OH, $C_1$-$C_3$alkyl, $C_1$-$C_3$alkoxy or CO—$OR_{46}$,
$R_{46}$ $C_1$-$C_3$alkyl;
$R_{42}$, $R_{43}$, $R_{44}$ and $R_{45}$ are the same or different and each is $C_1$-$C_3$alkyl, preferably $C_1$-$C_2$alkyl; or hydrogen;
Y is —NH—; or —O—; and
m is 0; or 1.

Specific examples of compounds of formula (32) are 4-methyl-3-penten-2-one, ethyl-3-methylamino-2-butenoate, 3-methylamino-1-phenyl-2-buten-1-one or 3-methylamino-1-phenyl-2-buten-1-one.

The class of cinnamic acid amide organic UV absorbers for example, corresponds to the formula:

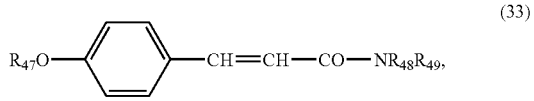

(33)

wherein
R$_{47}$ is hydroxy or C$_1$-C$_4$alkoxy, preferably methoxy or ethoxy;
R$_{48}$ is hydrogen or C$_1$-C$_4$alkyl, preferably methyl or ethyl; and
R$_{49}$ is —(CONH)$_m$-phenyl in which m is 0 or 1 and the phenyl group is optionally substituted by one, two or three substituents selected from OH, C$_1$-C$_3$alkyl, C$_1$-C$_3$alkoxy or CO—OR$_{50}$; and
R$_{50}$ is C$_1$-C$_4$alkyl.

The class of sulfonated benzimidazole organic UV absorbers for example corresponds to the formula

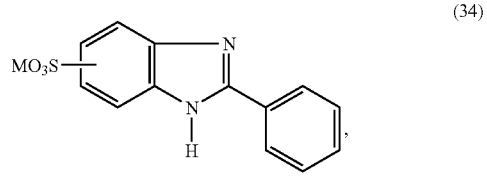

(34)

in which
M is hydrogen; or an alkali metal, preferably sodium, an alkaline earth metal, such as magnesium or calcium, or zinc.

Additional classes of water insoluble or slightly soluble UV absorbers used as the hydrophobic benefit agent are for example,
p-aminobenzoic acid derivatives, typically 2-ethylhexyl-4-dimethylaminobenzoate
salicylic acid derivatives, typically 2-ethylhexyl salicylate; homosalates; and isopropyl sylicylates;
benzophenone derivatives, typically 2-hydroxy-4-methoxybenzophenone;
dibenzoylmethane derivatives, typically 1-(4-tert-butylphenyl)-3-(4-methoxyphenyl)-propane-1,3-dione;
diphenylacrylates, typically 2-ethylhexyl-2-cyano-3,3-diphenylacrylate and 3-(benzo-furanyl)-2-cyanoacrylate;
3-imidazol-4-yl-acrylic acid and 3-imidazol-4-yl-acrylate;
benzofurane derivatives, preferably 2-(p-aminophenyl) benzofuran derivatives, disclosed in EP-A-582 189, U.S. Pat. No. 5,338,539, U.S. Pat. No. 5,518,713 and EP-A-613 893;
polymeric UV absorbers, such as the benzylidenemalonate derivatives described, inter alia in EPA-709 080;
cinnamic acid derivatives, typically the 2-ethylhexyl-4-methoxycinnamate or isoamylate or cinnamic acid derivatives disclosed, inter alia, in U.S. Pat. No. 5,601, 811 and WO 97/00851;
camphor derivatives, typically 3-(4'-methyl)benzylidenebornan-2-one, 3-benzylidenebornan-2-one, N-[2(and 4)-2-oxyborn-3-ylidenemethyl)benzyl]acrylamide polymer, 3-(4'-trimethylammonium)benzylidenebornan-2-one methylsulfate, 3,3'-(1,4-phenylenedimethine)-bis(7,7-dimethyl-2-oxobicyclo-[2.2.1]heptane-1-methanesulfonic acid) and the salts thereof, 3-(4'-sulfo)benzylidenebornan-2-one and the salts thereof;
2-phenylbenzimidazole-5-sulfonic acids and the salts thereof; and
menthyl-o-aminobenzoate.

The above classes of UV absorbers may be in a non-micronized, micronized, micronizable or oil form.

Regardless of the physical form of the UV absorber, these UV absorbers are water insoluble or slightly soluble in water. This physical form may actually convert a water soluble UVA to a water insoluble UVA. For example, micronizing the UVA may convert it to a water insoluble form.

If the UV absorber is micronized, it is preferably produced by the method described in U.S. Pat. No. 5,980,872, herein incorporated entirely by reference, namely by a process which comprises grinding the corresponding organic UV absorber, in coarse particle form, in a grinding apparatus, in the presence of 1 to 50%, preferably 5 to 40% by weight, based on the micronized organic UV absorber, of an alkyl polyglucoside having the formula C$_n$H$_{2n+1}$O (C$_6$H$_{10}$O$_5$)$_x$H, in which n is an integer ranging from 8 to 16 and x is the mean polymerization level of the glucoside moiety (C$_6$H$_{10}$O$_5$) and ranges from 1.4 to 1.6, or an ester thereof.

Thus micronized, insoluble organic UV absorbers, may be considered one of the hydrophobic benefit agents which may be deposited on skin by using the silicone cationic block copolymer as an aid. When the micronized UV absorber is used in combination with the block copolymer in sunscreen formulations, the combination provides excellent UV protection as well as wash-off protection and has at least as high an SPF rating as corresponding sunscreen formulations containing a known inorganic UV absorber.

The micronised formulation of an insoluble organic UV absorber, produced according to the method of U.S. Pat. No. 5,980,872 may be used together with one or more further UV absorbers, such as soluble organic UV absorbers, insoluble inorganic UV absorbers and/or melanine, which are conventionally used in cosmetic compositions for the protection of human skin against UV radiation. The use of such combinations of active ingredients may lead to synergistic effects.

Accordingly, the present invention also provides a sunscreen composition comprising a) 0.1 to 15%, preferably 0.5 to 10% by weight, based on the total composition of a micronised formulation of an insoluble organic UV absorber or oil soluble organic UV absorbers; and optionally b) a cosmetically acceptable carrier.

The sunscreen composition may be produced by physically blending the micronised formulation of an insoluble organic UV absorber and carrier components by any conventional method, e.g. by simply stirring the two materials together. The sunscreen composition may be formulated as a water-in oil or an oil-in-water dispersion, an oil or oil-alcohol lotion, a vesicular dispersion of an ionic or nonionic amphiphilic lipid, a gel, a solid stick or an aerosol formulation.

When formulated as a water-in oil or an oil-in-water dispersion, the optional cosmetically acceptable carrier preferably comprises 5 to 50% of an oil phase, 5 to 20% of an emulsifier and 30 to 90% of water, each by weight based on the total weight of the carrier.

Any known process suitable for the preparation of microparticles can be used for the preparation of the micronised UV absorbers, for example wet-milling, wet-kneading, spray-drying from a suitable solvent, by the expansion according to the RESS process (Rapid Expansion of Supercritical Solutions), by reprecipitation from suitable solvents, including supercritical fluids (GASR process=Gas Anti-Solvent Recrystallization/PCA process=Precipitation with Compressed Anti-solvents).

If the UV absorbers are micronized they usually have an average particle size from 0.02 to 2, preferably from 0.03 to 1.5, and more especially from 0.05 to 1.0 micrometer.

The micronizable UV absorbers can also be used as dry substrates in powder form or as an oil.

The organic water insoluble or slightly soluble sunscreens which are most preferred are those that are government approved for use on skin as sunscreen agent. These may for example be aminobenzoic acid, avobenzone, cinoxate, dioxybenzone, homosalate, menthyl anthranilate, octocrylene, octyl methoxycinnamate, octyl salicylate, oxybenzone, padimate O, phenylbenzimidazole sulfonic acid, sulisobenzone, or trolamine salicylate, a cinnamate derivative or an hydroxybenzotriazole such as Bisoctrizole, bisethylhexyloxyphenol methoxyphenol triazine or Bemotrizinol.

Hydrophobically Modified Pigment Particles

Hydrophobically modified pigment particles are also envisioned as hydrophobic benefit agents. In particular, pigment particles may be treated with hydrophobizing agents such as silicones and incorporated into body washes or rinse off compositions. For example U.S. Published Application No. 2004/0223929 discloses the use of hydrophobically modified pigments in rinsable compositions. Commercially available hydrophobized pigments for example may be purchased under the tradenames TIMIRON from US Cosmetics and KOBOPEARL from Kobo Product Inc.

Hydrophobized pigments such as effect pigments treated with a hydrophobizing coating are especially preferred. Effect pigments well known in the art are often formed most typically from inorganic platelet materials such as mica, glass or a reflecting material. The platelet is coated with a dielectric material such as $TiO_2$. The color of the platelet will be determined by the number of coating layers, the thickness of the dielectric material and the type of core (mica, glass or reflecting material). The final effect pigment is hydrophobized.

These hydrophobized pigments may be combined with the amphiphilic block copolymer described above which combination more readily deposits the pigments onto the skin and helps retain their deposition on skin after rinsing.

Co-pending U.S. application Ser. No. 11/903,595 herein incorporated entirely by reference discloses certain hydrophobized pigments such as cetyldimethicone coated pigments. These treated pigments may be combined with the amphiphilic block copolymer described above resulting in effective deposition of the hydrophobized pigments.

For a more complete but not exhaustive list of specific water insoluble hydrophobic benefit agents for keratinous substrates, such as fragrances, sunscreens (or ultraviolet light absorbers), skin care and hair care agents, please see U.S. Pat. No. 6,861,397 which lists found therein are incorporated entirely by reference.

The hydrophobic benefit agent weight percent of the total weight of the rinsable formulation will vary depending upon the type of benefit agent to be deposited. For example, a petrolatum is generally used in an amount from about 1 to about 50 wt. %, about 1 to about 25 wt. %, about 1 to about 20 wt. %, about 1 to about 15 wt. % or about 1 to about 10 wt. %.

If the hydrophobic benefit agent is a UV screening agent, the agent is present in the rinsable composition in amounts from about 0.01 weight % to about 50 weight % based on the weight of the total composition. Alternatively, the UV screening agent is present in the rinsable composition in amounts from about 0.1 weight % to about 30 weight % based on the weight of the total composition. Typically, UV screening agent is present in the rinsable composition in amounts from about 1 weight % to about 20 weight % based on the weight of the total composition. Typically, UV screening agent is present in the rinsable composition in amounts from about 1 weight % to about 5 weight % based on the weight of the total composition.

Particular sunscreen actives in a rinsable formulation may for example range in concentration as below:

| | |
|---|---|
| Octyl methoxycinnamate | about 2 to about 7 wt. % |
| Octyl salicylate | about 2 to about 5 wt. % |
| Avobenzone | about 1 to about 3 wt. % |
| Bisoctrizole | about 1 to about 10 wt. % |

The above UV screening agents in their micronized forms are particularly preferred.

If ester oils are the hydrophobic benefit agent, the total ester oil as a wt. % of the rinsable formulation will for example range from about 1 to about 20 wt. % or about 1 to about 15 wt. %.

The hydrophobic benefit agent, may comprise several hydrophobic benefit agents such as a sunscreen active and petrolatum. Other hydrophobic benefit agent mixtures may for example be combinations of fat soluble vitamins with sunscreen, several different sunscreens or fat soluble vitamins with ester oils.

If the hydrophobic benefit agent is a hydrophobized pigment, the pigments makes up no more than about 0.01 to about 20 wt. percent of the rinsable composition. For examples, the hydrophobized pigment may make up about 0.1 to about 10 wt. % or about 0.2 to about 5 wt. % rinsable composition.

A preferred list of hydrophobic benefit agents are for example, water insoluble or slightly water soluble
organic sunscreen agents or UV absorbers;
petrolatum;
ester oils;
ester oils that are predominantly comprised of triglycerides and modified triglycerides;
plant and seed extracts;
hydrophobized pigments;
vitamins and mixtures of the above.

The categories above are not absolute and are used for illustrative purposes. For example, there will be overlap between ester oils and ester oils that are predominantly comprised of triglycerides and modified triglycerides. Plant and seed extracts will normally include mixtures. The hydrophobic mixtures extracted may include some combination of for example, vitamins and ester oils. By way of example neem seed oil (Azadirachta indica) is a pressed vegetable oil from the fruits and seeds of Neem. It comprises mainly triglycerides and triterpenoids compounds. It also contains steroids.

The hydrophoibic benefit agent is different than the amphiphilic block copolymer.

Amphiphilic Block Copolymers

Amphiphilic block copolymers are normally defined as block copolymers comprising hydrophobic and hydrophilic blocks.

"Block copolymers" as used herein is meant to encompass two or more different polymeric units which are covalently linked to form a single polymer molecule. Typically, the block copolymers are in the form of di-, tri- and multi-block polymers. The block copolymers may be linear, grafted, structured, comb or star architecture.

The terms structured and unstructured is often used to refer to the crosslinking character of a formed polymer.

The amphiphilic block copolymer of the invention comprises at least two polymer blocks or segments.

A block may be defined by naming a polymer or by naming the monomers it is derived from.

For purposes of the invention, a monomer unit is defined as the unit formed after polymerization.

The term monomer by itself refers to the monomer before polymerization.

The term (meth)acrylate includes both acrylate and methacrylate derivatives.

The term (meth)acrylamide includes both acrylamide and methacrylamide derivatives. A block may be a copolymer, comprising several kinds of repeating units or monomer units, deriving from several monomers. Block A and block B are different polymers, deriving from different monomers, but they may comprise some common repeating units or monomer units (copolymers).

For purposes of the invention the term "polymer block" refers to one of the blocks of the block copolymer. The polymer block is either hydrophilic or hydrophobic. The polymer block may be random or made up multiple blocks.

For example, the block copolymer may be (a cationic polymer block-siloxane polymer block) diblock copolymer, a (cationic polymer block-siloxane polymer block-cationic polymer block) a triblock copolymer.

The terms "hydrophobic" and "hydrophilic," when applied to the block copolymers of this invention, are used in their ordinary sense. That is, hydrophilic, when it refers to a polymer, means that the polymer has a strong tendency to bond with or absorb water, which can result in solution of the polymer and/or swelling and/or formation of a gel. This property is characteristic of polymers prepared from polar or ionic monomers. Similarly, hydrophobic, when it refers to hydrophobic block, means that the polymer is antagonistic to water and generally cannot be dissolved in or swelled by water. This property is characteristic of polymers prepared from relatively non-polar monomers.

The amphiphilic block copolymer is soluble in water or may be dispersed in water.

The weight ratio of the siloxane block to cationic block will vary. The weight ratio for siloxane:cationic may vary from about 1:100 to about 100:1, for example about 1:10 to about 10:1 based on the total weight of the formed amphiphilic block copolymer. Additional weight ratios envisioned may be about 1:4 to about 4:1, about 1:3 to about 3:1, about 1:2 to about 2:1 or about 1:1.

The total molecular weight of the formed amphiphilic block copolymer will vary widely depending upon the application. For example, The average molecular weight for the amphiphilic block will for example range from about 500 g/mole to about 1,000,000 g/mole, about 500 g/mole to about 500,000 g/mole, about 800 g/mole to about 500,000 g/mole and more preferably from about 800 g/mole to 150,000 g/mole.

The repeat unit molar ratio of siloxane units to cationic units may vary widely. For example, about 1:100 to about 100:1, about 1:25 to about 25:1, about 1:10 to about 10:1 are envisioned of about 1:3 to about 3:1.

An excess of cationic units or siloxane units may be preferable.

The Cationic Block

By cationic polymer block, it is meant that the block is cationic at the conditions of use. Thus the cationic block may be formed from quaternary salts or from the corresponding amine which becomes protonated at the conditions of use.

The cationic block will contain at least monomer units represented by either formula (I) or (II).

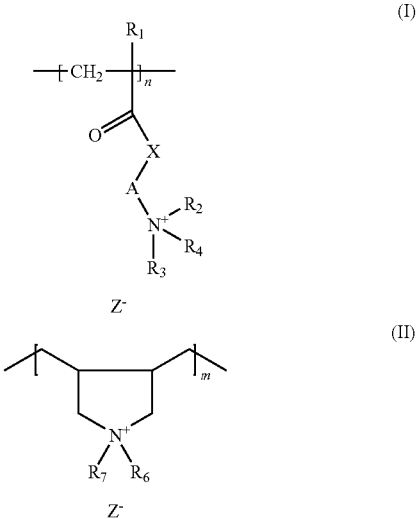

wherein $R_1$ is hydrogen or methyl, $R_2$ is hydrogen, a branched or unbranched $C_{1-4}$ alkyl, $R_3$ and/or $R_4$ are independently branched or unbranched $C_{1-22}$ alkyl, $C_1$-$C_4$ alkylhydroxy, benzyl or $R_3$ and $R_4$ can be combined to form a five or six membered ring with the nitrogen, said ring containing one or more hetero atoms, $Z^-$ is the conjugate base of an acid, X is oxygen or $NR_5$, wherein $R_5$ is as defined in $R_1$ above, A is an alkylene group of 1 to 4 carbons, $R_6$ and $R_7$ are hydrogen, branched or unbranched $C_{1-22}$ alkyl, benzyl or $C_1$-$C_4$ alkylhydroxy, n and m are 2, 3, 4 or greater.

Thus the hydrophilic (cationic) block of the amphiphilic block copolymer of the invention for example, may be derived from diallyalkylamines, aminoalkyl (meth)acrylates, aminoalkyl (meth)acrylamides monomers, their protonated salts or quaternary ammonium salts thereof.

Quaternized amines are well known in the art. The corresponding amines (before quaternization) of formula (I) and (II) may be alkylated to form the quaternary ammonium salt after formation of the hydrophilic polymeric block (A).

There are no particular limitations on the quaternizing agents that can be used to quaternized the tertiary amino groups of the hydrophilic block of the block copolymer. For example, the quaternizing agents may include alkyl halides such as methyl chloride, ethyl chloride, methyl bromide, ethyl bromide, methyl iodide, ethyl iodide and long chain alkyl halides such as $C_6$-$C_{24}$ alkyl halides; alkyl halide carboxylates such as sodium chloroacetate, sodium bromoacetate, and sodium iodoacetate, benzyl halides such as benzyl chloride, benzyl bromide and benzyl iodide, sulfonic acid ester derivatives such as dimethyl sulfate, diethyl sulfate, methyl o-toluene sulfonate, methyl p-toluene sulfonate, ethyl o-toluene sulfonate, ethyl p-toluene sulfonate, methyl methane sulfonate, ethyl methane sulfonate, methyl benzene sulfonate and ethyl benzene sulfonate.

The cationic block may be formed from diallylamine, then quaternized or the cationic block may be formed from diallydialkylammonium chloride directly. The cationic block may be formed from aminoalkyl (meth)acrylates or aminoalkyl (meth)acrylamides, then quaternized or the amphiphilic block may be formed from the quaternized monomers directly.

The quaternized derivatives are cationically charged regardless of the pH of use.

The hydrophilic block may also be formed from additional ethylenically unsaturated monomers which are ionic and/or nonionic, as long as the hydrophilic polymer block maintains its hydrophilic properties. The hydrophilic polymer block may also be grafted, random or further functionalized and/or crosslinked.

Representative examples of diallyalkylamines their protonated salts or quaternary ammonium salts are:
diallyldimethylammonium chloride (DADMAC), diallyldiethylammonium chloride, diallyldimethylammonium bromide, diallyldimethylammonium sulfate, diallyldimethylammonium phosphate, diallyldi(beta-ethoxyethyl) ammonium chloride and diallyldi(beta-hydroxyethyl) ammonium chloride.

Representative examples of aminoalkyl (meth)acrylates and aminoalkyl (meth)acrylamides monomers, their protonated salts or quaternary ammonium salts thereof are:
dimethylaminoethyl acrylate, dimethylaminoethylmethacrylate, dimethylaminoethyl acrylate methyl chloride quaternary salt, dimethylaminoethyl acrylate methyl sulfate quaternary salt, dimethylaminoethyl acrylate benzyl chloride quaternary salt, dimethylaminoethyl methacrylate methyl sulfate quaternary salt, dimethylaminoethyl methacrylate benzyl chloride quaternary salt, diethylaminoethyl acrylate, diethylaminoethyl methacrylate, diethylaminoethyl acrylate methyl chloride quaternary salt, diethylaminoethyl methacrylate methyl chloride quaternary salt, methacrylamidopropyldimethylamine, methacrylamidopropyltrimethylammonium chloride, acrylamidopropyldimethylamine, acrylamidopropyltrimethylammonium chloride and dimethylaminopropylacrylamide methyl sulfate quaternary salt.

The counterion of $Z^-$ may be virtually any counterion. $Z^-$ may be a counterion, represented by but not limited to chloride, bromide, iodide, substituted or unsubstituted aryl sulfonates, sulfate, alkyl sulfonates such as methyl sulfonate, ethyl sulfonate, carboxylates, nitrate, phosphates, tetrafluoroborate, tetraalkylborate, tetraarylborate, perchlorate, and hexafluorophosphate.

The cationic block may also contain other ethylenically unsaturated monomers. These monomers may be nonionic, anionic or zwitterionic. The cationic block may be formed from combinations of different cationic or potentially cationic monomer units. For example, both monomer units of formula (I) and formula (II) may be present in the cationic monomer block. Further, additional cationic monomer units not encompassed by formula (I) or (II) may also be incorporated into block (A).

More typically the cationic block will be formed from a homopolymer of formula (I) or (II).

Representative nonionic monomers or macromers are:
polymerizable allylic, vinylic and alpha ethylenically unsaturated compounds and are electrically neutral. Suitable nonionic monomers include acrylamide, methacrylamide, N-methyl(meth)acrylamide, N,N-dimethyl(meth)acrylamide, N-isopropyl(meth)acrylamide, N-(2-hydroxypropyl)(meth)acrylamide, poly(ethylene glycol)(meth)acrylate, poly(ethylene glycol) monomethyl ether mono(meth)acrylate, $C_{1-4}$ alkyl esters of (meth)acrylic acid such as methyl (meth)acrylate, ethyl(meth)acrylate, N-methylolacrylamide, N-vinylformamide, N-vinylacetamide, N-vinyl-N-methylacetamide, fumaramide, N-vinyl-2-pyrrolidone, glycerol mono((meth)acrylate), 2-hydroxyethyl(meth)acrylate, vinyl methylsulfone, vinyl acetate, diacetone acrylamide, diesters of maleic, fumaric, succinic and itaconic acids.

Representative anionic monomers or macromers are:
derived from alpha ethylenically unsaturated monomers selected from the groups consisting of alpha ethylenically unsaturated monomers containing phosphate or phosphonate groups, alpha ethylenically unsaturated monocarboxylic acids, monoalkylesters of alpha ethylenically unsaturated dicarboxylic acids, monoalkylamides of alpha ethylenically unsaturated dicarboxylic acids, alpha ethylenically unsaturated compounds comprising a sulphonic acid group, salts of alpha ethylenically unsaturated compounds comprising a sulphonic acid group and mixtures thereof.

Representative examples of anionic monomers include acrylic acid, methacrylic acid, vinyl sulphonic acid, salts of vinyl sulfonic acid, vinylbenzene sulphonic acid, salts of vinylbenzene sulphonic acid, alpha-acrylamidomethylpropanesulphonic acid, salts of alpha-acrylamidomethylpropanesulphonic acid, 2-sulphoethyl methacrylate, salts of 2-sulphoethyl methacrylate, acrylamido-2-methylpropanesulphonic acid (AMPS), salts of acrylamido-2-methylpropanesulphonic acid, maleic acid, fumaric acid, itaconic acid, succinic acid, styrenesulphonate and its salts or mixtures thereof.

The zwitterionic monomers are derived from ethylenically unsaturated monomers. A zwitterionic monomer for the purposes of the invention is defined as a monomer that contains both anionic and cationic charges.

Representative examples are
N,N-dimethyl-N-acryloyloxyethyl-N-(3-sulfopropyl)-ammonium betaine,
N,N-dimethyl-N-acryloyloxyethyl-N-(2-carboxymethyl)-ammonium betaine,
N,N-dimethyl-N-acrylamidopropyl-N-(3-sulfopropyl)-ammonium betaine,
N,N-dimethyl-N-acrylamidopropyl-N-(2-carboxymethyl)-ammonium betaine,
2-(methylthio)ethyl methacryloyl-S-(sulfopropyl)-sulfonium betaine,
2-[(2-acryloylethyl)dimethylammonio]ethyl 2-methyl phosphate,
2-(acryloyloxyethyl)-2'(trimethylammonium)ethyl phosphate,
[(2-acryloxyethyl)dimethylammonio]methyl phosphonic acid,
2-methacryloyloxyethyl phosphorylcholine (MPC),
2-[(3-acrylamidopropyl)dimethylammonio]ethyl 2'-isopropyl phosphate (AAPI),
1-vinyl-3-(3-sulfopropyl)imidazolium hydroxide,
(2-acryloxyethyl) carboxymethyl methylsulfonium chloride,
1-(3-sulfopropyl)-2-vinylpyridinium betaine,
N-(4-sulfobutyl)-N-methyl-N,N-diallylamine ammonium betaine (MDABS), N,N-diallyl-N-methyl-N-(2-sulfoethyl) ammonium betaine or mixtures thereof.

The cationic polymer blocks may be any average molecular weight. The preferred average molecular weight however will vary from about 500 g/mole to about 1,000,000 g/mole, about 500 g/mole to about 500,000 g/mole, about 800 g/mole to about 500,000 g/mole and more preferably from about 800 g/mole to 100,000 g/mole, for example, about 800 g/mole to about 10,000 g/mole or about 1,000 g/mole to about 5,000 g/mole.

Thus m and n are normally greater than 4, for example 2 to 1000, 2 to 100 or 4 to 50.

Siloxane Block

The hydrophobic block is derived from siloxane containing monomers which may be slightly soluble in water. The important attribute of the siloxane hydrophobic block is once it is formed, the resulting block is insoluble or not swellable in water. The hydrophobic or siloxane polymer block may be formed from additional ethylenically unsaturated monomers. The hydrophobic or siloxane polymer block may also be grafted, further functionalized and/or crosslinked.

The hydrophobic block may be grafted for example with the cationic A block. Thus the siloxane block may comprise siloxane monomer units of formula (III)

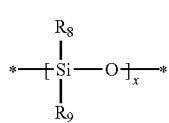

(III)

$R_8$ and $R_9$ are independently alkyl, phenylalkyl, alkoxy, aryl, aryloxy, alkylaryl, alkylamine, alkylhydroxy, polyoxyalkylene and polyalkylene polyamine or
—R-L-Polycationic Block,
wherein the Polycationic block is defined as block A above,
R is $C_1$ to $C_{10}$ alkylene, arylene, alkarylene or alkoxyalkylene,
L is a linking group,
and
x is and integer from 2 to 10,000.

A linking group as used herein is a —S— or —O—.

Alkyl is defined as linear or branched $C_1$-$C_{20}$. For example, alkyl may be $C_1$-$C_4$, $C_1$-$C_8$, $C_1$-$C_{12}$ or $C_1$-$C_{14}$.

$C_1$-$C_{20}$ alkyl is straight-chain or branched alkyl radicals, such as methyl, ethyl, n-propyl, iso-propyl, n-butyl, sec-butyl, tert-butyl, amyl, isoamyl or tert-amyl, heptyl, octyl, isooctyl, nonyl, decyl, undecyl, dodecyl, tetradecyl, pentadecyl, hexadecyl, heptadecyl, octadecyl or eicosyl.

For example, the siloxane block may be polydimethyl siloxane or polydiethylsiloxane. Polydimethylsiloxane is also known as dimethicone.

The siloxane block may be a homopolymer or a copolymer.

Methyl, ethyl and propyl or mixtures thereof are especially suitable as $R_8$ and $R_9$.

Aryl may be phenyl or alkyl substituted phenyl.

$C_1$-$C_{10}$ alkylene is for example a branched or unbranched radical, for example methylene, ethylene, propylene, trimethylene, tetramethylene, pentamethylene, hexamethylene, heptamethylene, octamethylene or decamethylene.

Arylene is for example substituted or unsubstituted phenylene or naphthylene each unsubstituted or substituted by $C_1$-$C_4$ alkyl is, for example, 1,2-, 1,3- or 1,4-phenylene or 1,2-, 1,3-, 1,4-, 1,6-, 1,7-, 2,6- or 2,7-naphthylene.

Alkyarylene is for example benzylidene and 2-phenylethylidene.

Alkoxyalkylene is for example alkylene interrupted by oxygen such as
—CH$_2$—O—CH$_2$—, —CH$_2$—O—CH$_2$CH$_2$—O—CH$_2$—,
—CH$_2$—(O—CH$_2$CH$_2$—)$_2$O—CH$_2$—, —CH$_2$—(O—CH$_2$CH$_2$—)$_3$O—CH$_2$— and
—CH$_2$—(O—CH$_2$CH$_2$—)$_4$O—CH$_2$—.

Acrylated silicones are known to enhance shine characteristics of hair having a refractive indices of about 1.46 or higher, especially about 1.52 or higher.

Polymethylphenylsiloxane is an example of an acrylated siloxane.

Alkylaryl may be for example, methyl, ethyl, t-butyl substituted phenyl.

Polyoxyalkylene is for example, polypropylene oxide and/or polyethylene oxide. The polyoxyalkylene may modify a polydialkylsiloxane. Alternatively, mixtures of alkylene oxides may be used to modify the base polysiloxane. For example polypropylene or polyethylene oxide may be used to modify polydimethylsiloxane. These materials are generally known as dimethicone copolyols. Thus the polysiloxane block may comprise dimethicone copolyols.

Alkoxy may be $C_1$-$C_4$ branched or linear alkoxy such as methoxy, ethoxy, propoxy and n-butoxy and t-butoxy.

Aryloxy may be for example, phenoxy or alkyl substituted phenoxy.

Alkylamines are for example, $C_1$-$C_4$ branched or linear alkyl radicals substituted by amines. The one or more amine substitution of the alkyl chain may occur anywhere on the chain such as at the end.

Alkylhydroxy $C_1$-$C_4$ branched or linear alkyl radicals substituted by hydroxy. The one or more hydroxy substitution of the alkyl chain may occur anywhere on the chain such as at the end.

Polyalkylenepolyamines are alkylene chains interrupted by amines.

For example, formula (IV) is representative of polyalkylenepolyamine substitution on a siloxane.

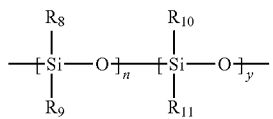

(IV)

The $R_8$, $R_9$ and n are defined as above and $R_{10}$ may be hydroxyl, $C_1$-$C_4$ alkoxy or $C_1$-$C_4$ alkyl, $R_{11}$ is —(CH$_2$)$_{1-4}$—NR$_{12}$—(CH$_2$)$_{1-4}$—NR$_{12}$R$_{13}$ and y is an integer from 1 to 10,000. $R_{12}$ and $R_{13}$ is the same or different and is hydrogen or $C_1$-$C_4$ alkyl.

The siloxane block of the amphiphilic block copolymer may for example be formula (IV).

When $R_8$ and $R_9$ are methyl, the above polymer (IV) is sometimes referred to as "amodimethicone".

References disclosing suitable siloxanes include U.S. Pat. No. 2,826,551, to Geen; U.S. Pat. No. 3,964,500, to Drakoff, issued Jun. 22, 1976; U.S. Pat. No. 4,364,837, to Pader; and British Patent No. 849,433, to Woolston, all of which are incorporated herein by reference in their entirety. Also incorporated herein by reference in its entirety is "Silicon Compounds" distributed by Petrarch Systems, Inc., 1984. This reference provides an extensive, though not exclusive, listing of suitable silicones.

The number of repeat units in the siloxane block (n) will vary from about 2 to about 10,000, for example, from about 10 to 5000 and from about 20 to about 1000.

The siloxane polymer block or segment may be formed from additional monomers. The additional monomers may or may not contain silicon. For example, all monomers making up the monomer units of the siloxane polymer block contain silicone.

The hydrophobic block even though it may contain additional monomer units other than siloxane containing units, the block should retain its characteristic hydrophobicity.

The siloxane block polymer may contain more than one siloxane block. For example, the siloxane block polymer may comprise a polydimethylsiloxane block and a polymethylphenylsiloxane block, or a polydivinylsiloxane block and a polydimethylsiloxane block.

The siloxane block may be for example, a polyalkyl siloxane, polyaryl siloxane, polyalkylaryl siloxanes, polyether siloxane copolymers and mixtures thereof.

The number of repeat units (n or y) in the siloxane block will vary from about 2 to about 10,000, for example, from about 10 to 5000 and about 20 to about 1000.

The average molecular weight for the siloxane block may be any average molecular weight. The siloxane polymer blocks may be for example, from about 500 g/mole to about 1,000,000 g/mole, about 500 g/mole to about 500,000 g/mole, about 800 g/mole to about 500,000 g/mole and more preferably from about 800 g/mole to 100,000 g/mole, for example, about 800 g/mole to about 10,000 g/mole or about 1,000 g/mole to about 5,000 g/mole.

Preparation of the Amphiphilic Block Copolymer

The Amphiphilic Block copolymer may be formed by polymerizing a cationic monomer or potentially cationic monomer in the presence of a suitably terminated polysiloxane.

Suitably terminated with a chain transfer group for purposes of the invention means termination or pendant termination with a thiol, xanthate, dithioester, trithioester, dithiocarbamate, secondary alcohol or nitroxyl. For example U.S. Pat. No. 6,858,696 discloses polysiloxanes derivatized with a xanthate herein incorporated entirely by reference.

A thiol terminated hydrophobic block may be synthesized by treating for example, polysiloxane resin having terminal double bonds or hydroxyl groups with such reagents as thioacetic acid, thiobenzoic acid, thiopropionic acid, thiobutyric acid, thiovaleric acid or secondary alcohol. The synthesis is described for example in Japanese Application No. 09031145 (1995) and Ying Jun Du et al. in *J. Applied Polymer. Sci.*, 2003, 594.

Polysiloxanes of various average molecular weights which are terminated with double bonds or hydroxyl groups are available commercially. For example, Siltech Coporation supplies a range of reactive polysiloxanes under the tradenames SILMER OH and SILMER VIN.

The block copolymer may then be directly formed by polymerizing the cationic monomer or potentially cationic monomer in the presence of an initiator and the suitably terminated polysiloxane block.

It is also possible that the polysiloxane block be grafted with pendant chain transfer groups such as thiols. The cationic monomer, for example DADMAC or diethylaminoethyl methacrylate or quaternary derivative, would then be polymerized in the presence of a polysiloxane polymer with thiol pendant groups, giving a grafted block copolymer with grafted cationic blocks.

For example, the block copolymer of formula (III) may be formed by polymerizing a thiol terminated polysiloxane in the presence of diallyldialkylammonium chloride.

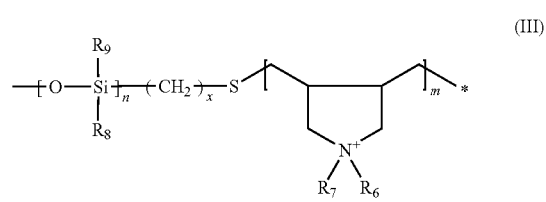

(III)

$R_6$ and $R_7$ are independently alkyl, phenylalkyl, alkoxy, aryl, aryloxy, alkylaryl;

For example, the block copolymer of formula (IV) may be formed by polymerizing a thiol terminated polysiloxane in the presence of trialkylammonium alkyl (meth)acrylate chloride.

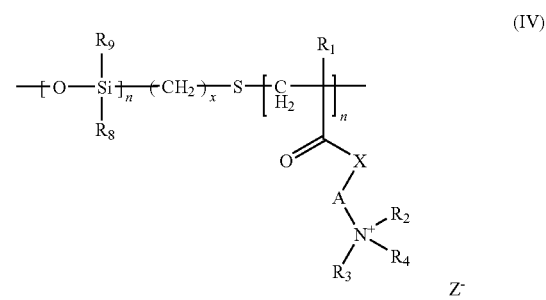

(IV)

Substituents are defined as above. Preferably $R_2$ is hydrogen, a branched or unbranched $C_{1-4}$ alkyl, The polymerization initiator can be any initiator such as those activated by heat, light or electromagnetic radiation or an oxidizing or reducing agent.

Typical initiators are for example, azobis compounds such as azobisisobutyronitrile, azobis-2,4-dimethylvaleronitrile, azobiscyclohexane carbonitrile, azobis-2-amidinopropane hydrochloride, dimethyl azobisisobutyrate, azobisisobutylamidine hydrochloride and 4,4'-azobis-4-cyanovaleric acid, peroxide initiators such as benzoyl peroxide, benzoyl 2,4-dichloroperoxide, di-tert-butyl peroxide, lauroyl peroxide, acetyl peroxide, diisopropyl dicarbonate peroxide, cumene hydroperoxide, tert-butyl hydroperoxide, dicumyl peroxide, p-menthane hydroperoxide, pinane hydroperoxide, methyl ethyl ketone peroxide, cyclohexanone peroxide, diisopropyl peroxy dicarbonate, tert-butyl peroxy laurate, di-tert-butyl peroxy phthalate, dibenzyl oxide and 2,5-dimethylhexane-2,5-dihydroperoxide, and redox initiators such as benzoyl peroxide-N,N-dimethyl aniline, peroxodisulfuric acid-sodium hydrogen sulfite and salts of persulfate such as sodium, potassium or ammonium persulfate.

Photoinitiators are also envisioned.

The reaction solvent includes, for example, aliphatic hydrocarbons such as pentane, hexane, heptane, octane, decane, dodecane and tetradecane, alicyclic hydrocarbons such as cyclopentane, methylcyclopentane, cyclohexane, methylcyclohexane, cyclooctane and cyclohexene, aromatic hydrocarbons such as benzene, toluene and xylene, halogenated hydrocarbons such as dichloromethane, chloroform, dichloroethane, dichloropropane, trichloroethylene, chlorobenzene, dichlorobenzene and 2,4-dichlorotoluene, esters such as methyl acetate, ethyl acetate and butyl acetate, ketones such as acetone and methyl ethyl ketone, and dioxane, tetrahydrofuran, acetonitrile, dimethylformamide, dimethyl sulfoxide and alcohols such as methanol, ethanol, propanol, isopropanol, n-butanol, isobutanol, sec-butanol, and t-butanol.

The addition of surfactants to the solvents is also envisioned.

These can be used alone or as a mixture thereof. Mixtures of solvents may be preferable.

Other Ingredients of the Delivery System or Rinsable Composition

The delivery system or rinsable composition must contain the amphiphilic block copolymer and at least one hydrophobic benefit agent. The weight ratio of i.) the amphiphilic block copolymer and ii.) the hydrophobic benefit agent will depend to some extent on the total formulation of the delivery system or rinsable composition. However the weight ratio of i.) to ii.) will range from about 1:30 to about 30:1. For example, about 1:20 to about 20:1, from about 1:10 to about 10:1, from about 1:5 to about 5:1, from about 1:2 to about 2:1 are typical.

The rinsable compositions will most typically contain at least some water. Preferably, the rinsable compositions will also contain an oil phase. Thus for example the composition may be an oil/water or water/oil emulsion.

Optional Ingredients

The compositions of the present invention may contain one or more additional skin care components. In a preferred embodiment, where the composition is to be in contact with human keratinous tissue, the additional components should be suitable for application to keratinous tissue, that is, when incorporated into the composition they are suitable for use in contact with human keratinous tissue without undue toxicity, incompatibility, instability, allergic response, and the like within the scope of sound medical judgment.

The CTFA Cosmetic Ingredient Handbook, Second Edition (1992) describes a wide variety of nonlimiting cosmetic and pharmaceutical ingredients commonly used in the personal care industry, which are suitable for use in the compositions of the present invention.

Additional components useful herein can be categorized by the benefit they provide or by their postulated mode of action. However, it is to be understood that the additional components useful herein can in some instances provide more than one benefit or operate via more than one mode of action. Therefore, classifications herein are made for the sake of convenience and are not intended to limit the active to that particular application or applications listed.

Structurants

The present compositions may optionally comprise an oil structurant. The structurant can provide a dispersed phase (should the composition embody a dispersed phase) with the correct rheological properties. This can aid in providing effective deposition and retention to the skin, the structured oil or oil phase should have a viscosity in the range of 100 to about 200,000 poise measured at 1 Sec-1

The structurant can be either an organic or inorganic structurant. Examples of organic thickeners suitable for the invention are solid fatty acid esters, natural or modified fats, fatty acid, fatty amine, fatty alcohol, natural and synthetic waxes, and petrolatum, and the block copolymers sold under the name KRATON by Shell. Inorganic structuring agents include hydrophobically modified silica or hydrophobically modified clay. Nonlimiting examples of inorganic structurants are BENTONE 27V, BENTONE 38V or BENTONE GEL MIO V from Rheox; and CAB-O-SIL TS720 or CAB-O-SIL M5 from Cabot Corporation.

Structurants meeting the above requirements with the selected skin compatible oil can form 3-dimensional network to build up the viscosity of the selected oils. It has been found that such structured oil phases, i.e., built with the 3-dimensional network, are extremely desirable for use as wet-skin treatment compositions used in bathing. These structured oils can deposit and be retained very effectively on wet skin and retained after rinsing and drying to provide long-lasting after wash skin benefit without causing a too oily/greasy wet and dry feel. It is believed that the highly desirable in-use and after-use properties of such structured oils are due to their shear thinning rheological properties and the weak structure of the network. Due to its high low-shear viscosity, the 3-dimensional network structured oil can stick and retain well on the skin during application of the skin conditioner. After being deposited on the skin, the network yields easily during rubbing due to the weak structuring of the crystal network and its lower high-shear viscosity.

Surfactants

A wide variety of surfactants can be useful herein, both for emulsification of the dispersed phase as well as to provide acceptable spreading and in use properties for non-lathering systems. For cleansing applications, the surfactant phase also serves to clean the skin and provide an acceptable amount of lather for the user. The composition contains for example, no more than about 50 weight percent of a surfactant, no more than about 30 weight percent, no more than about 15 weight percent, and more than about 5 weight percent of a surfactant. Typically, the composition contains at least about 5 weight percent of a surfactant, at least about 3 weight percent, at least about 1 weight percent, and at least about 0.1 weight percent of a surfactant.

Surfactants for example, include those selected from the group consisting of anionic surfactants, nonionic surfactants, amphoteric surfactants, non-lathering surfactants, emulsifiers and mixtures thereof. Non-limiting examples of surfactants useful in the compositions of the present invention are disclosed in U.S. Pat. No. 6,280,757, to McAtee et al., issued Aug. 28, 2001.

A) Anionic Surfactants

Non-limiting examples of anionic surfactants useful in the compositions of the present invention are disclosed in McCutcheon's, Detergents and Emulsifiers, North American edition (1986), published by allured Publishing Corporation; McCutcheon's, Functional Materials, North American Edition (1992); and U.S. Pat. No. 3,929,678, to Laughlin et al., issued Dec. 30, 1975.

A wide variety of anionic surfactants are useful herein. Non-limiting examples of anionic surfactants include those selected from the group consisting of sarcosinates, sulfates, isethionates, taurates, phosphates, lactylates, glutamates, and mixtures thereof.

Other anionic materials useful herein are fatty acid soaps (i.e., alkali metal salts, e.g., sodium or potassium salts) typically having from a fatty acid having about 8 to about 24 carbon atoms, preferably from about 10 to about 20 carbon atoms. These fatty acids used in making soaps can be obtained from natural sources such as, for instance, plant or animal-derived glycerides (e.g., palm oil, coconut oil, soybean oil, castor oil, tallow, lard, etc.) The fatty acids can also be synthetically prepared. Soaps and their preparation are described in detail in U.S. Pat. No. 4,557,853.

Other anionic materials include phosphates such as monoalkyl, dialkyl, and trialkylphosphate salts. Non-limiting examples of preferred anionic lathering surfactants useful herein include those selected from the group consisting of sodium lauryl sulfate, ammonium lauryl sulfate, ammonium laureth sulfate, sodium laureth sulfate, sodium trideceth sulfate, ammonium cetyl sulfate, sodium cetyl sulfate, ammonium cocoyl isethionate, sodium lauroyl isethionate, sodium lauroyl lactylate, triethanolamine lauroyl lactylate, sodium caproyl lactylate, sodium lauroyl sarcosinate, sodium myristoyl sarcosinate, sodium cocoyl sarcosinate, sodium lauroyl methyl taurate, sodium cocoyl methyl taurate, sodium lauroyl glutamate, sodium myristoyl glutamate, and sodium cocoyl glutamate and mixtures thereof.

Examples of typical surfactants are ammonium lauryl sulfate, ammonium laureth sulfate, sodium lauroyl sarcosinate, sodium cocoyl sarcosinate, sodium myristoyl sarcosinate, sodium lauroyl lactylate, and triethanolamine lauroyl lactylate.

B) Non-ionic Surfactants

Non-limiting examples of nonionic surfactants for use in the compositions of the present invention are disclosed in McCutcheon's, Detergents and Emulsifiers, North American edition (1986), published by allured Publishing Corporation; and McCutcheon's, Functional Materials, North American Edition (1992).

Nonionic surfactants useful herein include those selected from the group consisting of alkyl glucosides, alkyl polyglucosides, polyhydroxy fatty acid amides, alkoxylated fatty acid esters, sucrose esters, amine oxides, and mixtures thereof.

Non-limiting examples of preferred nonionic surfactants for use herein are those selected form the group consisting of $C_8$-$C_{14}$ glucose amides, $C_8$-$C_{14}$ alkyl polyglucosides, sucrose cocoate, sucrose laurate, lauramine oxide, cocoamine oxide and mixtures thereof.

C) Amphoteric Surfactants

The term "amphoteric surfactant," as used herein, is also intended to encompass zwitterionic surfactants, which are well known to formulators skilled in the art as a subset of amphoteric surfactants.

A wide variety of amphoteric lathering surfactants can be used in the compositions of the present invention. Particularly useful are those which are broadly described as derivatives of aliphatic secondary and tertiary amines, preferably wherein the nitrogen is in a cationic state, in which the aliphatic radicals can be straight or branched chain and wherein one of the radicals contains an ionizable water solubilizing group, e.g., carboxy, sulfonate, sulfate, phosphate, or phosphonate.

Non-limiting examples of amphoteric surfactants useful in the compositions of the present invention are disclosed in McCutcheon's, Detergents and Emulsifiers, North American edition (1986), published by allured Publishing Corporation; and McCutcheon's, Functional Materials, North American Edition (1992).

Non-limiting examples zwitterionic surfactants are those selected from the group consisting of betaines, sultaines, hydroxysultaines, alkyliminoacetates, iminodialkanoates, aminoalkanoates, and mixtures thereof.

Typical surfactants for use herein are the following, wherein the anionic surfactant is selected from the group consisting of ammonium lauroyl sarcosinate, sodium trideceth sulfate, sodium lauroyl sarcosinate, ammonium laureth sulfate, sodium laureth sulfate, ammonium lauryl sulfate, sodium lauryl sulfate, ammonium cocoyl isethionate, sodium cocoyl isethionate, sodium lauroyl isetlionate, sodium cetyl sulfate, sodium lauroyl lactylate, triethanolamine lauroyl lactylate, and mixtures thereof, wherein the non-ionic surfactant is selected from the group consisting of lauramine oxide, cocoamine oxide, decyl polyglucose, lauryl polyglucose, sucrose cocoate, $C_{12}$-$_{14}$ glucosamides, sucrose laurate, and mixtures thereof; and wherein the amphoteric surfactant is selected from the group consisting of disodium lauroamphodiacetate, sodium lauroamphoacetate, cetyl dimethyl betaine, cocoamidopropyl betaine, cocoamidopropyl hydroxy sultaine, and mixtures thereof.

D) Non-Lathering Surfactants

A wide variety of non-lathering surfactants are useful herein. The composition of the present invention can comprise a sufficient amount of one or more non-lathering surfactants to emulsify a dispersed phase (if the composition has a dispersed phase) to yield an appropriate particle size and good application properties on wet skin.

Nonlimiting examples of these non-lathering compositions are: polyethylene glycol 20 sorbitan monolaurate (Polysorbate 20), polyethylene glycol 5 soya sterol, Steareth-20, Ceteareth-20, PPG-2 methyl glucose ether distearate, Ceteth-10, Polysorbate 80, cetyl phosphate, potassium cetyl phosphate, diethanolamine cetyl phosphate, Polysorbate 60, glyceryl stearate, PEG-100 stearate, polyoxyethylene 20 sorbitan trioleate (Polysorbate 85), sorbitan monolaurate, polyoxyethylene 4 lauryl ether sodium stearate, polyglyceryl-4 isostearate, hexyl laurate, steareth-20, ceteareth-20, PPG-2 methyl glucose ether distearate, ceteth-10, diethanolamine cetyl phosphate, glyceryl stearate, PEG-100 stearate, and mixtures thereof.

E) Emulsifier Systems

The present rinsable compositions or delivery systems may be emulsions, gels, stable dispersions, liquids or soaps. In the event, the composition is an emulsion, there are several commercial emulsifier mixtures that may be useful in some embodiments. Examples include PROLIPID 141 (glyceryl stearate, behenyl alcohol, palmitic acid, stearic acid, lecithin, lauryl alcohol, myristyl alcohol and cetyl alcohol) and 151 (Glyceryl stearate, cetearyl alcohol, stearic acid, 1-propanamium, 3-amino-N-(2-(hydroxyethyl-)—N—N-Dimethyl,N—C(16-18) Acyl Derivatives, Chlorides) from ISP; POLAWAX NF (Emulsifying wax NF), INCROQUAT BEHENYL TMS (behentrimonium sulfate and cetearyl alcohol) from Croda; and EMULLIUM DELTA (cetyl alcohol, glyceryl stearate, peg-75 stearate, ceteth-20 and steareth-20) from Gattefosse.

Thickening/Aqueous Phase Stability Agents

The compositions of the present invention, in some embodiments, may further include one or more thickening/aqueous phase stability agents. Because different stability agents thicken with different efficiencies, it is difficult to provide an accurate compositional range, however, when present, the composition preferably comprises no more than about 10 weight percent Nonlimiting examples of thickening agents useful herein include carboxylic acid polymers such as the carbomers (such as those commercially available under the tradename CARBOPOL® 900 series from B.F. Goodrich; e.g., CARBOPOL® 954). Other suitable carboxylic acid polymeric agents include copolymers of C.sub.10-30 alkyl acrylates with one or more monomers of acrylic acid, methacrylic acid, or one of their short chain (i.e., C.sub.1-4 alcohol) esters, wherein the crosslinking agent is an allyl ether of sucrose or pentaerytritol. These copolymers are known as acrylates/C.sub.10-30 alkyl acrylate crosspolymers and are commercially available as CARBOPOL® 1342, CARBOPOL® (1382, PEMULEN TR-1, and PEMULEN TR-2, from B.F. Goodrich.

Other nonlimiting examples of thickening agents include crosslinked polyacrylate polymers including both cationic and nonionic polymers.

Still other nonlimiting examples of thickening agents include the polyacrylamide polymers, especially nonionic polyacrylamide polymers including substituted branched or unbranched polymers. More preferred among these polyacrylamide polymers is the nonionic polymer given the CTFA designation polyacrylamide and isoparaffin and laureth-7, available under the Tradename SEPIGEL 305 from Seppic Corporation (Fairfield, N.J.). Other polyacrylamide polymers useful herein include multi-block copolymers of acrylamides and substituted acrylamides with acrylic acids and substituted acrylic acids. Commercially available examples of these multi-block copolymers include HYPAN SR150H, SS500V, SS500W, SSSA100H, from Lipo Chemicals, Inc., (Patterson, N.J.).

Another nonlimiting class of thickening agents useful herein are the polysaccharides. Nonlimiting examples of polysaccharide gelling agents include those selected from cellulose, and cellulose derivatives. Preferred among the alkyl hydroxyalkyl cellulose ethers is the material given the CTFA designation cetyl hydroxyethylcellulose, which is the ether of cetyl alcohol and hydroxyethylcellulose, sold under the tradename NATROSEL® CS PLUS from Aqualon Corporation (Wilmington, Del.). Other useful polysaccharides include scleroglucans which are a linear chain of (1-3) linked glucose units with a (1-6) linked glucose every three units, a commercially available example of which is CLEAROGEL.™. CS 11 from Michel Mercier Products Inc. (Mountainside, N.J.).

Another nonlimiting class of thickening agents useful herein are the gums. Nonlimiting examples of gums useful herein include hectorite, hydrated silica, xantham gum, and mixtures thereof.

Yet another nonlimiting class of thickening agents useful herein are the modified starches. Acrylate modified starches such as WATERLOCK® from Grain Processing Corporation may be used. Hydroxypropyl starch phosphate, tradename STRUCTURE XL from National Starch is another example of a useful modified starch, and other useful examples include ARISTOFLEX HMB (Ammonium Acrylodimethyltaruate/Beheneth—25 Methacrylate Crosspolymer) from Clariant and cationic stabylens.

Cationic Polymers

The present invention may also contain organic cationic deposition polymer Concentrations of the cationic deposition polymer may range from none to about 0.025% to about 3%, from about 0.05% to about 2%, and from about 0.1% to about 1%, by weight of the personal care composition.

Suitable cationic deposition polymers for use in the present invention contain cationic nitrogen-containing moieties such as quaternary ammonium or cationic protonated amino moieties. The cationic protonated amines can be primary, secondary, or tertiary amines (preferably secondary or tertiary), depending upon the particular species and the selected pH of the personal cleansing composition.

Nonlimiting examples of cationic deposition polymers for use in the personal care composition include polysaccharide polymers, such as cationic cellulose derivatives. Preferred cationic cellulose polymers are the salts of hydroxyethyl cellulose reacted with trimethyl ammonium substituted epoxide, referred to in the industry (CTFA) as Polyquatemium 10 which are available from Amerchol Corp. (Edison, N.J., USA) in their Polymer KG, JR and LR series of polymers with the most preferred being KG-30M.

Other suitable cationic deposition polymers include cationic guar gum derivatives, such as guar hydroxypropyltrimonium chloride, specific examples of which include the Jaguar series (preferably Jaguar C-17) commercially available from Rhodia Inc., and N-Hance polymer series commercially available from Aqualon.

Other suitable cationic deposition polymers include synthetic cationic polymers. The cationic polymers suitable for use in the cleansing composition herein are water soluble or dispersible, non crosslinked, cationic polymers having a cationic charge density of from about 4 meq/gm to about 7 meq/gm and an average molecular weight of from about 1,000 to about 1 million.

The concentration of the cationic polymer in the personal care composition ranges from about 0.025% to about 5%, preferably from about 0.1% to about 3%, more preferably from about 0.2% to about 1%, by weight of the composition.

A non limiting example of a commercially available synthetic cationic polymer for use in the cleansing compositions is polymethyacrylamidopropyl trimonium chloride, available under the trade name POLYCARE 133, from Rhodia, Cranberry, N.J., U.S.A.

Other Optional Ingredients

Other non limiting examples of optional ingredients include benefit agents that are selected from the group consisting of vitamins and derivatives thereof (e.g., ascorbic acid, vitamin E, tocopheryl acetate, and the like); sunscreens; thickening agents (e.g., polyol alkoxy ester, available as CROTHIX from Croda); preservatives for maintaining the anti microbial integrity of the cleansing compositions; anti-acne medicaments (resorcinol, salicylic acid, and the like); antioxidants; skin soothing and healing agents such as aloe vera extract, allantoin and the like; chelators and sequestrants; and agents suitable for aesthetic purposes such as fragrances, essential oils, skin sensates, pigments, pearlescent agents (e.g., mica and titanium dioxide), lakes, colorings, and the like (e.g., clove oil, menthol, camphor, eucalyptus oil, and eugenol), antibacterial agents and mixtures thereof. These materials can be used at ranges sufficient to provide the required benefit, as would be obvious to one skilled in the art.

EXAMPLES

The following examples further describe and demonstrate embodiments within the scope of the invention. The examples are given solely for the purpose of illustration and are not to be construed as limiting the invention. Other variations are possible without departing from the spirit and scope of the invention.

All percents represent weight % of the total unless specified otherwise.

ABBREVIATIONS

SPF refers to Sun Protection Factor.
SILMER® VIN 100 vinyl terminated dimethylsilicone prepolymer of about 4400 to 6000 $M_n$.
DADMAC Diallydimethylammonium chloride supplied by CIBA Corp. Tarrytown, N.Y.,
FM1 Dimethylaminoethyl methacrylate supplied by CIBA Corp., Tarrytown, N.Y.
VITRO-SKIN® mimics the surface properties of human skin. It contains both protein and lipid components and is designed to have topography, pH, critical surface tension and ionic strength similar to human skin. The substrate is currently used by over 155 leading companies worldwide and has been referenced in numerous scientific presentations and patents. It has been successfully applied in a broad range of in vitro methods including the measurement of sun protection factor (SPF). The term in vitro skin is used interchangeable with the tradename VITRO-SKIN® herein.

TINOSORB® M Bisoctrizole/Micronized-insoluble in water

OMC Octinoxate $M_n$ Number Average Molecular Weight.

Synthesis of Block or Grafted Block Copolymers

Example 1-5

Linear Triblock Copolymer

Conversion of Vinyl End-Functional Polysiloxane into Thiol 20 g vinyl end-functional polydimethylsiloxane (Silmer VIN 100, Siltech) is dissolved in 20 mL toluene. To this is added 550 mg azobisisobutyronitrile and 0.8 mL thioacetic acid. The mixture is sparged with nitrogen for 30 min, then heated at 80° C. for 6 h. It is cooled in ice/water and rinsed with methanol three times. The residual solvent is removed under vacuum.

15 g of the product is dissolved in 20 mL toluene, and 2 mL 10% methanolic sodium hydroxide is added. The mixture is sparged with nitrogen and stirred for 8 h. It is rinsed with methanol 3 times. The residual solvent is removed under vacuum.

Example 2

To a solution of 25 g vinyl end-functional polydimethylsiloxane (Silmer VIN 200, Siltech) in 20 mL toluene is added 413 mg azobisisobutyronitrile and 0.6 mL thioacetic acid. The mixture is sparged with nitrogen for 30 min, then heated at 80° C. for 7 h. It is allowed to cool and rinsed with methanol three times. The residual solvent is removed under vacuum. To a solution of 2.0 g of this product in 2 ml ether that had been kept on lithium aluminum hydride (LAH) is added 50 mg LAH, and the mixture is stirred at room temperature for 48 h. The mixture is then filtered, and the solvent is removed under vacuum.

Example 3

Conversion of Hydroxyl End-Functional Polydimethylsiloxane into Thiol 20 g hydroxyl end-functional polydimethylsiloxane (Silmer OH100, Siltech) is dissolved in 50 mL dichloromethane. To this is added 2 mL pyridine and 4.0 g p-toluenesulfonyl chloride. The mixture is stirred at room temperature for 24 h. The product is rinsed with methanol 3 times, and the residual solvent is removed under vacuum.

g of the product is dissolved in 15 mL toluene and a solution of 0.45 g potassium thioacetate in 1.5 mL methanol is added. The mixture is sparged with nitrogen for 30 min., then stirred at 105° C. for 24 h. The mixture is allowed to cool, then rinsed with methanol 3 times, and the residual solvent is removed under vacuum. The product is dissolved in 10 mL toluene, and 1 mL 10% methanolic sodium hydroxide is added. The mixture is sparged for 30 min, then stirred for 8 h. It is rinsed with methanol 3 times, and the residual solvent is removed under vacuum.

Example 4

Synthesis of Block Copolymers of Polydimethylsiloxane and Diallyldimethylammonium Chloride (DADMAC)

A polymerization flask is charged with 4.0 g of the thiol end-functional polydimethylsiloxane of Example 1, 6.0 g dry DADMAC, 20 mL n-butanol, and 164 mg 2,2'-azobis (2-amidinopropane) dihydrochloride. After the DADMAC had dissolved, the mixture is sparged with nitrogen for 30 min, then heated and stirred at 70° C. for 24 h. It is allowed to cool. The product is precipitated with acetone and filtered. The white solid is dried in vacuum overnight. The product is stirred in 100 mL THF for 1 h, then filtered, rinsed with THF and dried in vacuum.

Examples 5-9

Several additional amphiphilic triblock copolymer of polysiloxane and DADMAC are synthesized similarly to example 4 but varying the average molecular weight of the starting polysiloxane and polydimethylsiloxane (vinyl terminated). Triblock copolymers of polydimethylsiloxane and polyDADMAC were formed as shown below in Table I.

Example 10

Grafted Block Copolymer

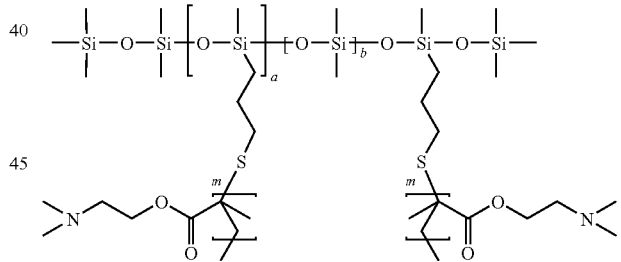

To a mixture of (Mercaptopropyl)methylsiloxane-dimethylsiloxane copolymer (SMS-022, 2-3 mol % SH, Gelest, Inc. 1 equiv.) and Dimethylaminoethyl methacrylate (FM1, Ciba, 100 equiv.) in THF is added 2,2'-azobisisobutyronitrile (AIBN, 1.2 equiv.). The solution is purged with nitrogen for 0.5 hr and is reacted at 70° C. for overnight. Polymer is recovered by evaporation of solvent.

TABLE 1

BLOCK COPOLYMERS OF SILOXANE AND DADMAC

| Example # | Silicone Block $M_n$ | PolyDADMAC Block MW | Total MW of Block or Grafted Block Copolymer | Si:DADMAC or Si:FM1 | Wt. % Si |
|---|---|---|---|---|---|
| 5 | 4400a | 4400 | 13200 | 0.50:1 | 14 |
| 6 | 4400 | 3700 | 11800 | 0.59:1 | 17 |

TABLE 1-continued

BLOCK COPOLYMERS OF SILOXANE AND DADMAC

| Example # | Silicone Block $M_n$ | PolyDADMAC Block MW | Total MW of Block or Grafted Block Copolymer | Si:DADMAC or Si:FM1 | Wt. % Si |
|---|---|---|---|---|---|
| 7 | 4400 | 2800 | 10000 | 0.80:1 | 21 |
| 8 | 6000 | 2400 | 10800 | 1.24:1 | 29 |
| 9 | 6000 | 1200 | 8400 | 2.44:1 | 44 |

APPLICATION EXAMPLES

Delivery of Sunscreen or Petrolatum onto VITRO-SKIN® and Residual Retained after Rinsing Example 11

Sunscreen is post added to commercially available body washes at a concentration (as is) of 4 weight % that corresponds to 2 weight % of sun screen active. The siloxane/cationic (in conditions of use) block copolymers are also post added to the body washes at different concentrations. VITRO-SKIN® is utilized as the keratinous substrate that effectively mimics the surface properties of human skin.

Example 12

A Typical Body Wash Formulation

Sodium Laureth Sulfate (Standapol Es-3) 20-30 wt. %
Cocamidopropyl Betaine 2-5%
Peg-6 caprylic/capric glyceride 3-6%
Glycerin 3-5%
Lauryl Glucoside and Sodium Laureth Sulfate 8-12%
Mineral Oil 2-10%
Petrolatum 2-10%
Preservative 0.05-1%
Water qs to 100%

The amphiphilic block copolymer may be added to the above body wash formulation at about 1 to 5 wt. %.

Determination of Sunscreen Residual Left on VITRO-SKIN®

The following laboratory equipment is used:
VITRO-SKIN® N-19, Foam block, Hydration Chamber, Powder Free Rubber Finger Cots and Glassless slide mounts are obtained from IMS, Inc. (70 Robinson Blvd, Orange, Conn., USA);
Water bath (#05-719-7F), Corning Hotplate Stirrer (#11-497-8A), Calfamo Compact Digital Stirrer (#14-500-7), Glycerol Aqueous Solution (#AC277366-0010) are obtained from Fisher Scientific Catalog; and
Optometrics SPF 290 is obtained from Optometrics LLC. (8 Nemco Way, Stony Brook Industrial Park, Ayer, Mass., USA).

Substrate (VITRO-SKIN®) Preparation

VITRO-SKIN® (N-19, Lot 6243) is pre-cut into 4.1×4.1 cm pieces and placed in a closed, controlled-humidity chamber for 16-22 hours prior to the tests. The humidity in the chamber is regulated by the 14.7% aqueous solution of glycerin placed in the bottom of the chamber. The substrate is placed above the liquid on a shelf. This step insures reproducible hydration of the substrate prior to product application.

A piece of hydrated substrate is placed in a glassless slide mount and allowed to dry for 15 minutes followed by test product application and rinse-off procedure. Product application is made to the "skin topograph" side of the substrate that is placed on a parafilm-covered foam block.

A separate piece of substrate treated in a similar manner but without test formulation application and rinsing is used as the reference for the in vitro SPF measurement.

Optometrics SPF 290S is turned on followed by the manufacturer's directions for instrument calibration, blank and sample measurements.

Test Formulation Application to In Vitro Skin

Onto each piece of substrate 0.18 g of test formulation (from example 11) is dispensed using a transfer pipette and a balance. Test formulation is applied to the substrate using a circular motion for about 20 seconds using a finger cot.

After application substrate is immediately placed in a glassless slide and rinsed with water using a water bottle. Rinsing time is 15 seconds. After rinse-off substrates are air-dried for about 15 minutes followed by SPF measurements in vitro as described briefly below. At least three slides are used for each test formulation.

The SPF measurements are made using an Optometrics SPF-290 from the Optometrics Group. A reference scan is run on the untreated VITRO-SKIN® from the same sheet of film which is used for the test formulations and has been pre-hydrated in a similar fashion. The "skin topograph" side of the VITRO-SKIN should be up. Each test formulations slide is placed above the integrating sphere. A minimum of five consecutive measurements are taken on five separate areas of each test slide. The reference scan is repeated for each additional slide tested.

Determination of Residual Petrolatum on VITRO-SKIN®

The presently described method determines the amount of petrolatum deposited on In vitro skin by following transepidermal water loss (TEWL) from VITRO-SKIN® (N-19). The amphiphilic block copolymers in combination with petrolatum formulations are applied to the VITRO-SKIN® substrate. Measurement of water loss indicates the effectiveness of deposition of petrolatum onto the in vitro skin from a leave-on or rinse-off formulation. Effectiveness of a compositions ability to insure residual petrolatum remaining on the skin after rinsing can also be determined in the same way.

The VITRO-SKIN® (N-19) is pre-cut into 6.3×6.3 cm pieces and placed in a closed, controlled-humidity chamber for 16-22 hours prior to the tests. The humidity in the chamber is regulated by the 14.7% aqueous solution of Glycerin placed in the bottom of the chamber. The substrate is placed above the liquid on a shelf. This step insures reproducible hydration of the VITRO-SKIN® prior to product application.

TEWL measurements are taken using a Delfin VapoMeter probe or cyberDERM RG1 Evaporimeter probe. VITRO-SKIN® substrate is prepared according to the procedure described above. A piece of hydrated substrate is mounted in a glassless slide and air-dried for 15 min. It is used as a reference for untreated VITRO-SKIN during the TEWL measurements. Test formulations containing amphiphilic block copolymer with petrolatum are applied on the "skin topography" side of the VITRO-SKIN placed on plastic-covered foam block at the same test sample application dose. Petrolatum, a known occlusive agent, is also used for each trial as a reference point by applying 2 mg/sq.cm, or exactly 0.07938 g to the substrate. Immediately after test formulations application, the formulations are rubbed into the film with a finger covered with fingercot.

After that the film is placed in a slide mounted and air-dried for about 15 min. Extra care is taken to assure that the rough side is up and the film is flat. The mounted substrate is placed into the testing chamber, along with the untreated substrate and the petrolatum treated substrate. Each substrate is then measured using either Cyberderm or Delfin probes after an initial 15 minutes, one half hour and one hour after application. Standard operating procedure are followed for each probe. Measurements are only taken when the climate temperature is between 20-22° C. and the relative humidity ranged between 20%-30%.

The same procedure above may be applied to VITRO-SKIN® treated with wash-off (rinse-off) test formulations containing petrolatum and amphiphilic block copolymers but rinsing the treated in vitro skin samples and determining the resulting TEWL.

The Standard is the substrate, in-vitro skin, treated with a known amount of petrolatum. This is used to determine a semi-quantitative assumption of how much petrolatum remains on the surface after rinse-off.

TABLE 2

SUNSCREEN DEPOSITION ON SKIN AFTER WASH OFF

| Commercial Body Wash | SPF on VITRO-SKIN® | STDV of SPF | UVA/UVB Ratio[2] | Boots Star Rating[3] | CW[4] nm |
|---|---|---|---|---|---|
| [1]DBW + 4% TINOSORB M | 1.33 | 0.16 | 0.664 | 3 | 381.2 |
| | 1.25 | 0.07 | 0.858 | 4 | 382.9 |
| | 1.12 | 0.02 | 0.546 | 2 | 380.3 |
| DBW + 4% TINOSORB M + Block Copolymer of example 6 | 2.08 | 0.1 | 0.94 | 5 | 383.5 |
| | 3.34 | 1.07 | 0.849 | 4 | 383.4 |
| | 2.47 | 0.13 | 0.91 | 5 | 383.7 |

[1]Commercially available Dove Fresh Moisture Body Wash. The body wash contains: Water, Helianthus Annuus (Sunflower) Seed Oil or Glycine Soja (Soybean) Oil, Sodium Laureth Sulfate, Sodium Lauroamphoacetate or Cocamodopropyl Betaine, Glycerin, Petrolatum, Lauric Acid, Cocamide MEA, Guarhydroxypropyltrimonium Chloride, Lanolin Alcohol, Citric Acid, DMDM Hydantoin and Tetrasodium EDTA.

[2] and [3]The Boot's Star Rating is the Star Rating (UVA/UVB Ratio) according to the Boots Star Rating System (5 star category). The Star Rating is calculated as an indicator of the UVA absorbance properties of a sunscreen product, relative to UVB as described in the Revised Guidelines to the practical measurement of UVA:UVB ratios according to the Boots Star Rating System. The calculation of the UVA:UVB absorbance ratio will typically yield values from zero (eaual to no UVA absorbance) up to 1.0 (UVA absorbance equal to UVB).

[4]The absorption spectrum of a sunscreen is characterized by an index, namely the critical wavelength (CW), which is the wavelength where the intrgral of the spectral absorbance curve reaches 90% of the integral from 290 nm to 400 nm. This value (CW) is used to determine the breadth of UV protection and is the recommended method for the evaluation of long wave efficacy of sunscreen products. See Diffey, BL, (1994), Intl J. Cosmet Sci., 16: 47-52 for further details.

Clearly the addition of the block copolymer in combination with the hydrophobic UV screening agent helps to retain residual SPF left on skin after washing. Thus the inventive block copolymers causes better deposition of the hydrophobic UV agent on skin and/or prevents removal from skin of the UV agent once exposed to washing or rinsing.

The inventive block copolymer may also be used in sunscreen formulations.

Example 13

Sunscreen Composition Preparation

| Part | Trade name | INCI name | Function | % W/W* |
|---|---|---|---|---|
| A | Arlacel 165 | Glyceryl Stearate (and) PEG-100 Stearate | Emulsifier, non-ionic | 3.50 |
| | Lanette 16 | Cetyl Alcohol | Emulsion Stabilizer | 1.00 |
| | Cetiol B | Dibutyl Adipate | Emollient/solvent | 5.00 |
| | Cetiol CC | Dicaprylyl Carbonate | Emollient/solvent | 5.00 |
| | Tegosoft DEC | Diethylhexyl Carbonate | Emollient/solvent | 2.00 |
| | Neo Heliopan AV | Octinoxate | Sunscreen Active | 7.50 |
| | Neo Heliopan OS | Octisalate | Sunscreen Active | 2.00 |
| | Parsol 1789 | Avobenzone | Sunscreen Active | 3.00 |
| | Tinosorb ® S | Drug name (proposed): Bemotrizinol; INCI name: Bis-Ethylhexyloxyphenol Methoxyphenyl Triazine | Sunscreen Active | 1.50 |
| | Orgasol 2002 EXD NAT COS | Nylon-12 | Spherical Particulate to improve skin feel | 1.50 |
| B | Water | Water | Diluent/solvent | Qs to 100.00 |
| | Keltrol CG RD | Xanthan Gum | Rheology Modifier | 0.22 |
| | Glycerin | Glycerin | Humectant | 3.00 |
| | Dissolvine NA2 | Disodium EDTA | Chelating Agent | 0.20 |
| C | Dow Corning 345 Fluid | Cyclopentasiloxane | Emollient/Solvent | 2.00 |
| | Tinovis ADM | Sodium Acrylates Copolymer (and) Mineral Oil (and) PPG-1 Trideceth-6 | Rheology Modifier | 0.83 |
| | Tinosorb ® M | Drug name (proposed): Bisoctrizole; INCI name: Methylene Bis- | Sunscreen Active | 3.00 (as is) or 1.50 (active level) |

-continued

| Part | Trade name | INCI name | Function | % W/W* |
|---|---|---|---|---|
| | Phenonip | Benzotriazolyl Tetramethylbutylphenol Phenoxyethanol (and) Methylparaben (and) Ethylparaben (and) Butylparaben (and) Propylparaben (and) Isobutylparaben | Preservative | 1.00 |
| | Sodium Hydroxide | Sodium Hydroxide (15% aqueous solution) | pH adjuster | Qs to pH ~5.3-6.1 |

*The components are added to the sunscreen composition on a % weight/weight of component (as active) based on the weight of the total composition.

Combine the ingredients of part A. Heat up part A to 80° C. with mixing. Mix until uniform, and add Nylon-12 with moderate agitation.

Prepare part B: first, disperse Xanthan Gum into the water and heat up to 80° C. When uniform, add the rest of part B one by one, mix until uniform.

Add part A into part B under stirring, and then homogenize with an Ultra Turrax pos 2 for 40 sec/100 g.

Cool down under stirring, to 40° C. and add the ingredients of part C one by one in the given order. Mix until uniform. If necessary, adjust pH with aqueous solution of sodium sydroxide to 5.3-6.1

The base sunscreen composition of Example 13 is formulated with about 1 to 5 wt. % of the block copolymer of Example 6.

Residual SPF after rinsing or washing is improved.

We claim:

1. A cosmetically acceptable delivery system for hydrophobic benefit agents to a keratinous substrate, wherein the delivery system comprises:
   i.) a linear non-crosslinked amphiphilic block copolymer formed by polymerizing a thiol terminated polysiloxane in presence of diallyldialkylammonium chloride, wherein the linear non-crosslinked amphiphilic block copolymer is a block copolymer of formula (III)

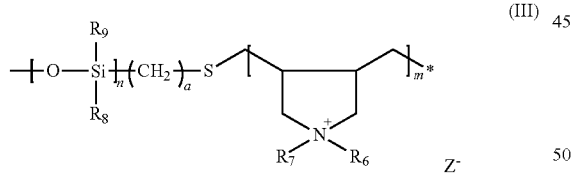

(III)

wherein:
$Z^-$ is a conjugate base of an acid;
$R_6$ and $R_7$ are hydrogen, branched or unbranched $C_{1-22}$ alkyl, benzyl, or $C_1$-$C_4$ alkylhydroxy;
$R_8$ and $R_9$ are independently $C_{1-4}$ alkyl, phenylalkyl, alkoxy, aryl, aryloxy, alkylaryl, or alkylamine;
n and m are 4 to 50; and
a is from 1 to 12; and
ii.) a hydrophobic benefit agent, wherein the hydrophobic benefit agent is an organic sunscreen agent and the organic sunscreen agent is micronized.

2. The delivery system according to claim 1, wherein the sunscreen agent is bisoctrizole.

3. The delivery system according to claim 1, wherein the delivery system further contains an anionic surfactant.

4. The delivery system according to claim 1, wherein average molecular weight of the linear non-crosslinked amphiphilic block copolymer ranges from about 500 g/mole to about 1,000,000 g/mole.

5. The delivery system according to claim wherein the keratinous substrate is hair, skin, finger nails, or toe nails.

6. The delivery system according to claim 1, wherein repeat unit molar ratio of siloxane units to cationic units is 1:3 to 3:1.

7. The delivery system according to claim 6, wherein the linear non-crosslinked amphiphilic block copolymer comprises a cationic block and a siloxane block and total molecular weight of the linear non-crosslinked amphiphilic block copolymer is from 500 g/mole to 500,000 g/mole.

8. The delivery system according to claim 7, wherein average molecular weight of the cationic block is from 1,000 g/mole to 10,000 g/mole.

9. The delivery system according to claim 8, wherein average molecular weight of the siloxane block is from 1,000 g/mole to 10,000 g/mole.

10. The delivery system according to claim 1, wherein about 1 to about 50 wt. % of the hydrophobic benefit agent applied to the keratinous substrate is retained after the delivery system is rinsed from the keratinous substrate.

11. The delivery system according to claim 1, wherein the hydrophobic benefit agents retard decrease in water content from skin or hair.

12. A body rinsable composition comprising a cosmetically acceptable delivery system for hydrophobic benefit agents to a keratinous substrate, wherein the delivery system comprises:
   i.) a linear non-crosslinked amphiphilic block copolymer formed by polymerizing a thiol terminated polysiloxane in presence of diallyldialkylammonium chloride, wherein the linear non-crosslinked amphiphilic block copolymer is a block copolymer of formula (III)

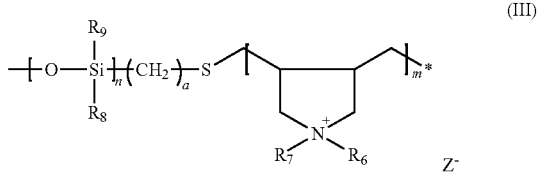

(III)

wherein:
$Z^-$ is a conjugate base of an acid;
$R_6$ and $R_7$ are hydrogen, branched or unbranched $C_{1-22}$ alkyl, benzyl, or $C_1$-$C_4$ alkylhydroxy;

$R_8$ and $R_9$ are independently $C_{1-4}$ alkyl, phenylalkyl, alkoxy, aryl, aryloxy, alkylaryl, or alkylamine;

n and m are 4 to 50; and a is from 1 to 12; and ii.) a hydrophobic benefit agent.

13. The body rinsable composition according to claim 12, wherein the hydrophobic benefit agent is selected from the group consisting of:

organic sunscreen agents or UV absorbers;

petrolatum;

ester oils;

ester oils that are predominantly comprised of triglycerides and modified triglycerides;

plant and seed extracts;

hydrophobic modified pigment particles;

vitamins; and any mixture of the above.

14. The body rinsable composition according to claim 12, wherein the body rinsable composition is a body wash, shower cream, shower gel, liquid soap, or a bar soap.

15. The body rinsable composition according to claim 12, wherein repeat unit molar ratio of siloxane units to cationic units is 1:3 to 3:1.

16. The body rinsable composition according to claim 15, wherein total molecular weight of the linear non-crosslinked amphiphilic block copolymer is from 500 g/mole to 500,000 g/mole.

17. The body rinsable composition according to claim 16, wherein the linear non-crosslinked amphiphilic block copolymer comprises a cationic block and a siloxane block, average molecular weight of the cationic block is from 1,000 g/mole to 10,000 g/mole, and average molecular weight of the siloxane block is from 1,000 g/mole to 10,000 g/mole.

18. The body rinsable composition according to claim 12, wherein the hydrophobic benefit agent is an organic sunscreen agent and the organic sunscreen agent is micronized.

19. The body rinsable composition according to claim 12, wherein about 1 to about 50 wt. % of the hydrophobic benefit agent applied to the keratinous substrate is retained after the body rinsable composition is rinsed from the keratinous substrate.

20. The body rinsable composition according to claim 12, wherein the hydrophobic benefit agents retard decrease in water content from skin or hair.

\* \* \* \* \*